(12) United States Patent
Rousseau et al.

(10) Patent No.: US 8,940,892 B2
(45) Date of Patent: Jan. 27, 2015

(54) TRIAZINE DERIVATIVES FOR USE IN THE TREATMENT OF MALARIA

(75) Inventors: Amanda Louise Rousseau, Dunvegan (ZA); David Gravestock, Ravenswood (ZA); Anna Catharina Uys Lourens, Pretoria (ZA)

(73) Assignee: CSIR, Pretoria (ZA)

( * ) Notice: Subject to any disclaimer, the term of this patent is extended or adjusted under 35 U.S.C. 154(b) by 180 days.

(21) Appl. No.: 13/390,017

(22) PCT Filed: Aug. 6, 2010

(86) PCT No.: PCT/IB2010/053570
§ 371 (c)(1),
(2), (4) Date: Feb. 10, 2012

(87) PCT Pub. No.: WO2011/018742
PCT Pub. Date: Feb. 17, 2011

(65) Prior Publication Data
US 2012/0142920 A1   Jun. 7, 2012

(30) Foreign Application Priority Data
Aug. 13, 2009   (ZA) ................................ 2009/05637

(51) Int. Cl.
C07D 251/10   (2006.01)
A61K 31/53   (2006.01)
A61P 33/06   (2006.01)
C07C 279/26   (2006.01)
C07D 251/18   (2006.01)

(52) U.S. Cl.
CPC ............... *A61K 31/53* (2013.01); *C07C 279/26* (2013.01); *C07D 251/18* (2013.01)
USPC .......................................... 544/208; 514/245

(58) Field of Classification Search
CPC ..... C07D 251/10; C07D 251/72; A61K 31/53
USPC .......................................... 544/208; 514/245
See application file for complete search history.

(56) References Cited

U.S. PATENT DOCUMENTS 3,287,365 A * 11/1966 Newman et al. ............... 544/206

FOREIGN PATENT DOCUMENTS

WO   WO 96/05841 A1   2/1996

OTHER PUBLICATIONS

Hunt, S.Y. et al. 2005 "Identification of the optimal third generation antifolate against *P. falciparum* and *P. vivax*" *Molecular and Biochemical Parasitology* 144: 198-205.
Jensen, N.P. et al. 2001 "Phenoxypropoxybiguanides, prodrugs of DHFR-inhibiting diaminotriazine antimalarials" *J Med Chem* 44(23): 3925-3931.
Lombardino, J.G. 1963 "4,6-diamino-l-alkyl-1,2-dihydro-s-triazines" *J Med Chem* 6: 213-214.
Selassie, C.D. et al. 1986 in *Chemisty and Biology of Pteridines*, B.A. Cooper and V.M Whitehead, eds, New York, "The Structure Activity Relationships of Novel Triazine Antifolates," pp. 959-962.

* cited by examiner

*Primary Examiner* — Venkataraman Balasubramanian
(74) *Attorney, Agent, or Firm* — Knobbe, Martens, Olson & Bear, LLP

(57) ABSTRACT

The invention provides compounds of formula (I), in which $R^1$ and $R^2$ are independently selected from H, alkyl, aryl and heteroaryl, or $R^1$ and $R^2$ together form a $C_5$-$C_7$ ring, $R^3$-$R^7$ are independently selected from H, halogen, alkyl and alkoxy, X is $(CH_2)n$ in which n is 0-5, Y is selected from $CH_2$, $NR^8$, O or S in which $R^8$ is H or alkyl, salts thereof and stereoisomers thereof, for the prophylaxis or treatment of malaria.

9 Claims, 3 Drawing Sheets

TRIAZINE DERIVATIVES FOR USE IN THE TREATMENT OF MALARIA

Figure 1:
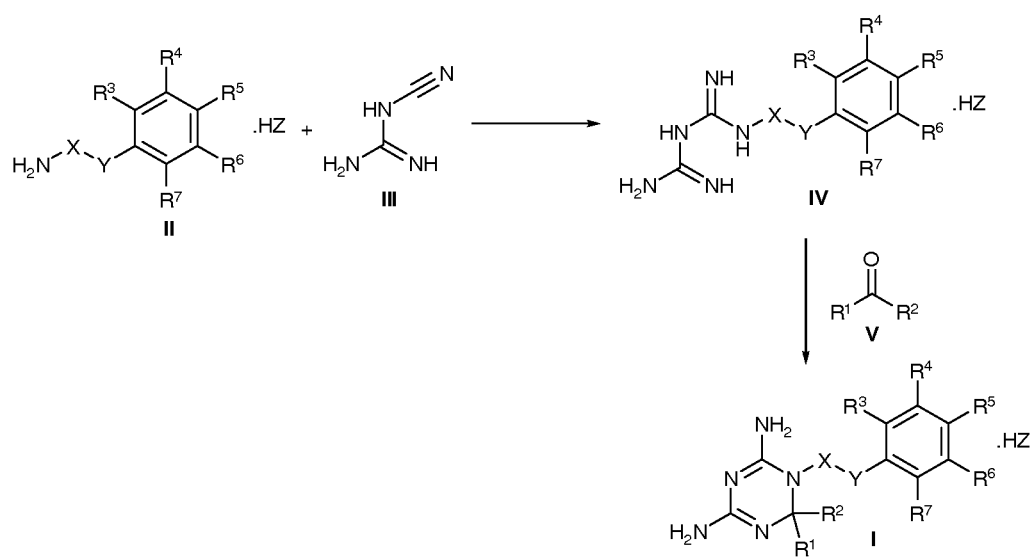

THIS invention relates to compounds which show activity against drug sensitive and drug resistant strains of *Plasmodium falciparum*. In particular, the invention relates to compounds which show activity against strains of *Plasmodium falciparum* which are resistant to chloroquine, cycloguanil and other antifolates.

Dihydrofolate reductase (DHFR; EC. 1.5.1.3) is an enzyme found in nearly all living cells, with only few exceptions.[1] The DHFR domain of the bifunctional *Plasmodium falciparum* dihydrofolate reductase-thymidylate synthase (PfDHFR-TS) is one of the few well-defined, validated targets in malarial chemotherapy.[2] The enzyme catalyses the nicotinamide adenine dinucleotide phosphate (NADPH) dependent reduction of 7,8-dihydrofolate (DHF) to 5,6,7,8-tetrahydrofolate (THF). Tetrahydrofolate and other reduced folates are essential cellular cofactors required by the parasite for the initiation of protein synthesis, and the biosynthesis of deoxythymidylate (dTMP), purine nucleotides, methionine and other essential metabolites. The malaria parasite relies heavily on these cofactors for growth, and is able to produce the required folate derivates de novo or via a folate salvage pathway.

PfDHFR, which maintains adequate levels of THF in both the de novo and salvage pathways, is the target of the most widely used antifolates, pyrimethamine (Pyr) and cycloguanil (CG), for prophylaxis and treatment of *P. falciparum* infection. It has been shown that resistance to these drugs develops through point mutations at various amino acid residues surrounding the PfDHFR active site, compromising the clinical utilities of these drugs. Despite this, the folate pathway remains a good target for chemotherapy because the enzyme is limited in its mutational capability, owing to loss in enzyme function.

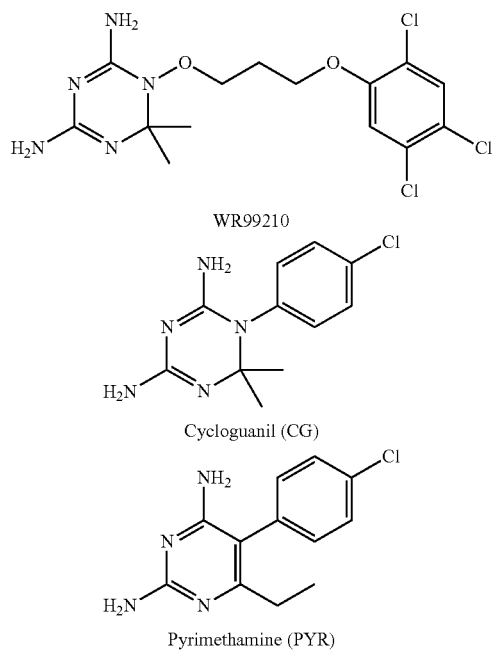

There is evidence to suggest that antifolates with greater structural flexibility are more effective against *P. falciparum* strains resistant to Pyr and CG.[3, 4] WR99210 contains a flexible linker between the two aromatic residues, and it is believed that this flexibility is responsible for the exceptional activity of this compound, which is effective in vitro in concentrations in the nanomolar (nM) range, even against strains that are highly resistant to other DHFR inhibitors. Unfortunately, WR99210 exhibits unacceptable gastrointestinal (GI) tolerability in mammalian systems. A biguanide precursor known as PS-15 was developed as a prodrug for WR99210 to avoid the GI intolerance, but has been abandoned due to cross-resistance with cycloguanil and pyrimethyamine.[5]

Although numerous authors have remarked on the importance of developing antifolates with flexible linkers to target drug resistant malaria, very few examples have been reported in the literature to date, with largely only analogues of WR99210 described.[6, 7] With the exception of two compounds, all of these analogues possess the N—O (or related N—S) linkage from the dihydrotriazine ring. With the exception of two compounds (which possess the N—O linkage from the dihydrotriazine ring), all bear a 2,2-dimethyl substitution pattern on the dihydrotriazine ring. Variations in the length of the flexible linker are reported for only three compounds, all of which bear the 2,2-dimethyl substitution pattern on the dihydrotriazine ring.

Other related compounds that have been reported in the literature that do not bear the N—O linkage from the dihydrotriazine ring include a series of 1-benzyl dihydrotriazines which were prepared as actives in a herbicidal composition[5], and a series of 2,2-dimethyl dihydrotriazines[9-11] some of which were prepared as actives in an insecticidal composition.[11]

It is accordingly an object of the present invention to provide 1,2-dihydro-1,3,5-triazine-4,6-diamines of general formula I, and pharmaceutically acceptable salts and formulations thereof, having antimalarial activity, including activity against drug-resistant malaria. It is a further object of the invention to provide methods for synthesizing 1,2-dihydro-1,3,5-triazine-4,6-diamines of general formula I, and pharmaceutically acceptable salts thereof.

According to a first aspect of the invention, there is provided a compound of formula I,

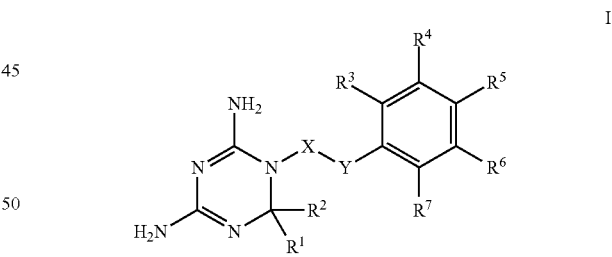

in which
$R^1$ and $R^2$ are independently selected from H, alkyl, aryl and heteroaryl, or $R^1$ and $R^2$ together form a $C_5$-$C_7$ ring,
$R^3$-$R^7$ are independently selected from H, halogen, alkyl and alkoxy,
X is $(CH_2)_n$ in which n is 0-5,
Y is selected from $CH_2$, $NR^8$, O or S in which $R^8$ is H or alkyl, salts thereof and stereoisomers thereof,
in which
"alkyl" means a group selected from
  $C_1$-$C_7$ straight chain alkyl groups, optionally substituted with one or more F, Cl, Br, O, S or N, and
  $C_1$-$C_7$ branched alkyl groups optionally substituted with one or more F, Cl, Br, O, S or N, "aryl" means a group selected from
  phenyl, and
  phenyl substituted with one or more F, Cl, Br, S, N, $C_1$-$C_7$ alkoxy, nitrile, trifluoromethyl, $C_1$-$C_7$ straight chain alkyl groups and $C_1$-$C_7$ branched alkyl groups, the alkyl groups being optionally substituted with one or more F, Cl, Br, O, S or N, "heteroaryl" means a group selected from thiophenyl, furyl, pyridinyl, isoxazolinyl, pyrrolinyl, oxazolinyl, thiazolinyl, imidazolyl which is optionally substituted with one or more F, Cl, Br, S, N, $C_1$-$C_7$ alkoxy, nitrile, trifluoromethyl, $C_1$-$C_7$ straight chain alkyl groups and $C_1$-$C_7$ branched alkyl groups, the alkyl groups being optionally substituted with one or more F, Cl, Br, O, S or N, "halogen" means F, Cl or Br, and "alkoxy" means a $C_1$-$C_7$ alkoxy group, provided that:

(1) when $R^1$ and $R^2$ are both methyl, X is $(CH_2)_n$, n is 2-5 and Y is O, then $R^3$-$R^7$ are not all H, (2) when $R^1$ and $R^2$ are independently selected from H, methyl, isopropyl, cyclohexyl, phenyl, 4-fluorophenyl, 4-chlorophenyl, 3,4-methylenedioxyphenyl, 4-acetamidophenyl, 4-methylthiophenyl or $R^1$ and $R^2$ together form —$(CH_2)_2CH(CH_3)$—$(CH_2)_2$—, X is $(CH_2)_n$, n is 0-3 and Y is $CH_2$, then $R^3$-$R^7$ are not all H for the prophylaxis or treatment of malaria.

The malaria may be of the type which is resistant to antifolate compounds. The antifolate compounds may be cycloguanil or pyrimethamine.

The salt may be the salt of any pharmaceutically suitable acid such as hydrochloric acid, picric acid, nitric acid or acetic acid.

The invention extends to the biguanide precursors of the compounds of formula I as prodrugs to improve bioavailability.

The halogen may be chlorine.

In preferred embodiments of the invention, $R^1$ is hydrogen, $R^2$ is selected from aryl, $R^3$ to $R^7$ are selected from hydrogen, halogen, alkyl and alkoxy; X is $(CH_2)_n$ where n is 0 or 1, Y is methylene and $R^3$-$R^7$ cannot all be H;

$R^1$ is hydrogen, $R^2$ is selected from aryl, $R^3$ to $R^7$ are selected from hydrogen, halogen, alkyl and alkoxy; at least one of $R^3$ to $R^7$ is chlorine, X is $(CH_2)_n$ where n is 0 or 1 and Y represents methylene;

$R^1$ is hydrogen, $R^2$ is selected from aryl, $R^3$ to $R^7$ are selected from hydrogen, halogen, alkyl and alkoxy; X is $(CH_2)_n$ where n is 2 to 5 and Y is oxygen;

$R^1$ is hydrogen, $R^2$ is selected from aryl, $R^3$ to $R^7$ are selected from hydrogen, halogen, alkyl and alkoxy; at least one of $R^3$ to $R^7$ is chlorine, X is $(CH_2)_n$ where n is 2 to 5 and Y is oxygen;

$R^1$ and $R^2$ are independently selected from hydrogen, aryl and heteroaryl, $R^5$ is chlorine and $R^4$ is selected from hydrogen atom and chlorine, X is a straight-chain alkyl group containing up to 5 carbon atoms, and Y is selected from methylene, nitrogen, oxygen and sulphur;

$R^1$ and $R^2$ are selected from hydrogen, aryl and heteroaryl, $R^3$ to $R^7$ are selected from hydrogen, halogen, alkyl and alkoxy; X is $(CH_2)_n$ where n is 0 to 5, Y is selected form $CH_2$, O, S and $NR^8$ and $R^8$ is selected from hydrogen and alkyl.

Preferred compounds of the invention include the compounds 1-(3,4-Dichlorobenzyl)-6-phenyl-1,6-dihydro-1,3,5-triazine-2,4-diamine hydrochloride, 1-(4-Chlorophenethyl)-6-phenyl-1,6-dihydro-1,3,5-triazine-2,4-diamine hydrochloride, 1-(3,4-Dichlorophenethyl)-6-phenyl-1,6-dihydro-1,3,5-triazine-2,4-diamine hydrochloride, 1-(2-(4-Chlorophenoxy)ethyl)-6-phenyl-1,6-dihydro-1,3,5-triazine-2,4-diamine hydrochloride, 1-(2-(3,4-Dichlorophenoxy)ethyl)-6-phenyl-1,6-dihydro-1,3,5-triazine-2,4-diamine hydrochloride, 1-(3-(4-Chlorophenoxy)propyl)-6-phenyl-1,6-dihydro-1,3,5-triazine-2,4-diamine hydrochloride, 1-(3-(3,4-Dichlorophenoxy)propyl)-6-phenyl-1,6-dihydro-1,3,5-triazine-2,4-diamine hydrochloride, 1-(3-(2,4-Dichlorophenoxy)propyl)-6-phenyl-1,6-dihydro-1,3,5-triazine-2,4-diamine hydrochloride, 6-Phenyl-1-(3-(3-(trifluoromethyl)phenoxy)propyl)-1,6-dihydro-1,3,5-triazine-2,4-diamine hydrochloride, 1-(3-(4-Methoxyphenoxy)propyl)-6-phenyl-1,6-dihydro-1,3,5-triazine-2,4-diamine hydrochloride, 1-(3-(2-Fluorophenoxy)propyl)-6-phenyl-1,6-dihydro-1,3,5-triazine-2,4-diamine hydrochloride, 1-(3-(2-Chlorophenoxy)propyl)-6-phenyl-1,6-dihydro-1,3,5-triazine-2,4-diamine hydrochloride, 1-(3-(4-Fluorophenoxy)propyl)-6-phenyl-1,6-dihydro-1,3,5-triazine-2,4-diamine hydrochloride, 6-Phenyl-1-(3-(4-(trifluoromethyl)phenoxy)propyl)-1,6-dihydro-1,3,5-triazine-2,4-diamine hydrochloride, 1-(3-(4-Chlorophenoxy)propyl)-6-(2-chlorophenyl)-1,6-dihydro-1,3,5-triazine-2,4-diamine hydrochloride, 1-(3-(4-Chlorophenoxy)propyl)-6-(4-(trifluoromethyl)phenyl)-1,6-dihydro-1,3,5-triazine-2,4-diamine hydrochloride, 1-(3-(4-Chlorophenoxy)propyl)-6-(4-methoxyphenyl)-1,6-dihydro-1,3,5-triazine-2,4-diamine hydrochloride, 6-(4-Chloro-3-fluorophenyl)-1-(3-(4-chlorophenoxy)propyl)-1,6-dihydro-1,3,5-triazine-2,4-diamine hydrochloride, 1-(3-(4-Chlorophenoxy)propyl)-6-(3-chlorophenyl)-1,6-dihydro-1,3,5-triazine-2,4-diamine hydrochloride, 1-(3-(4-Chlorophenoxy)propyl)-6-(4-fluorophenyl)-1,6-dihydro-1,3,5-triazine-2,4-diamine hydrochloride, 1-(3-(4-Chlorophenoxy)propyl)-6-(2-fluorophenyl)-1,6-dihydro-1,3,5-triazine-2,4-diamine hydrochloride, 1-(3-(4-Chlorophenoxy)propyl)-6-(2-(trifluoromethyl)phenyl)-1,6-dihydro-1,3,5-triazine-2,4-diamine hydrochloride, 1-(3-(3,4-Dichlorophenoxy)propyl)-6-(4-(trifluoromethyl)phenyl)-1,6-dihydro-1,3,5-triazine-2,4-diamine hydrochloride, 1-(3-(3,4-Dichlorophenoxy)propyl)-6-(2-(trifluoromethyl)phenyl)-1,6-dihydro-1,3,5-triazine-2,4-diamine hydrochloride, 1-(3-(3,4-Dichlorophenoxy)propyl)-6-(2-fluorophenyl)-1,6-dihydro-1,3,5-triazine-2,4-diamine hydrochloride, 1-(3-(3,4-Dichlorophenoxy)propyl)-6-(4-fluorophenyl)-1,6-dihydro-1,3,5-triazine-2,4-diamine hydrochloride, 6-(4-Chloro-3-fluorophenyl)-1-(3-(3,4-dichlorophenoxy)propyl)-1,6-dihydro-1,3,5-triazine-2,4-diamine hydrochloride, 6-(2-Chlorophenyl)-1-(3-(3,4-dichlorophenoxy)propyl)-1,6-dihydro-1,3,5-triazine-2,4-diamine hydrochloride, 1-(3-(4-Chlorophenoxy)propyl)-6-(4-chlorophenyl)-1,6-dihydro-1,3,5-triazine-2,4-diamine hydrochloride, 6-(3-Chloro-2-fluorophenyl)-1-(3-(4-chlorophenoxy)propyl)-1,6-dihydro-1,3,5-triazine-2,4-diamine hydrochloride, 6-(4-Chlorophenyl)-1-(3-(3,4-dichlorophenoxy)propyl)-1,6-dihydro-1,3,5-triazine-2,4-diamine hydrochloride, 6-(3-Chloro-2-fluorophenyl)-1-(3-(3,4-dichlorophenoxy)propyl)-1,6-dihydro-1,3,5-triazine-2,4-diamine hydrochloride,
1-(3-(4-Chlorophenoxy)propyl)-6-(2,5-dichlorophenyl)-1,6-dihydro-1,3,5-triazine-2,4-diamine hydrochloride,
1-(3-(4-Chlorophenoxy)propyl)-6-(2-fluoro-3-methoxyphenyl)-1,6-dihydro-1,3,5-triazine-2,4-diamine hydrochloride,
1-(3-(4-Chlorophenoxy)propyl)-6-(2,4-difluorophenyl)-1,6-dihydro-1,3,5-triazine-2,4-diamine hydrochloride,
1-(3-(4-Chlorophenoxy)propyl)-6-(2,4-dichlorophenyl)-1,6-dihydro-1,3,5-triazine-2,4-diamine hydrochloride,
1-(3-(4-Chlorophenoxy)propyl)-6-(3-(trifluoromethoxy)phenyl)-1,6-dihydro-1,3,5-triazine-2,4-diamine hydrochloride,
1-(3-(4-Chlorophenoxy)propyl)-6-m-tolyl-1,6-dihydro-1,3,5-triazine-2,4-diamine hydrochloride,
1-(3-(4-Chlorophenoxy)propyl)-6-(4-(trifluoromethylthio)phenyl)-1,6-dihydro-1,3,5-triazine-2,4-diamine hydrochloride,
1-(3-(2-Methoxy-4-methylphenoxy)propyl)-6-phenyl-1,6-dihydro-1,3,5-triazine-2,4-diamine hydrochloride,
1-(3-(4-Bromophenoxy)propyl)-6-phenyl-1,6-dihydro-1,3,5-triazine-2,4-diamine hydrochloride,
1-(3-(4-Chloro-3-fluorophenoxy)propyl)-6-phenyl-1,6-dihydro-1,3,5-triazine-2,4-diamine hydrochloride,
1-(3-(3,4-Difluorophenoxy)propyl)-6-phenyl-1,6-dihydro-1,3,5-triazine-2,4-diamine hydrochloride,
6-(2-Chlorophenyl)-1-(4-(3,4-dichlorophenoxy)butyl)-1,6-dihydro-1,3,5-triazine-2,4-diamine, and
(5-(4-Chlorophenoxy)pentyl)-6-(4-(trifluoromethyl)phenyl)-1,6-dihydro-1,3,5-triazine-2,4-diamine hydrochloride.

According to a second aspect of the invention, there is provided a compound of formula I, as described above with the further proviso that:

(1) when $R^1$ is selected from H, trifluoromethyl, undecyl, tert-butyl or phenyl and $R^2$ is H or methyl, Y is $CH_2$ for $X=(CH_2)_n$ and n=0 and $R^5$ is H or chlorine, then $R^3$, $R^4$, $R^6$ and $R^7$ are not all H and when $R^4$ and $R^5$ are methoxy then not all of $R^3$, $R^6$ and $R^7$ are H, and (2) when $R^1$ and $R^2$ are both methyl, X is $(CH_2)_n$, n is 0-3 and Y is $CH_2$, then neither $R^3$ nor $R^7$ is H.

According to a third aspect of the invention, there is provided a pharmaceutical formulation which includes or comprises a compound as described above.

According to a fourth aspect of the invention, there is provided a substance or composition for use in a method of treatment or prophylaxis of malaria, in particular drug-resistant malaria, the substance or composition comprising a compound of formula I, as hereinbefore described.

It is a particular aspect of the present invention that the compounds of the invention have a flexible linker of variable length between the aromatic and dihydrotriazine rings but do not possess an N—O linkage as in the case of WR99210 and its analogues. Furthermore, the substituents at the 2-position on the dihydrotriazine ring include aryl, substituted aryl, heteroaryl, alkyl and substituted alkyl.

The compounds of the invention show activity against drug resistant strains of *Plasmodium falciparum*, including, but not limited to, the data shown in Table 1.

TABLE 1

| No. | Compound | Antimalarial activity (FCR-3) Mean $IC_{50}$ (μM) | Cytotox SRB (HeLa) $IC_{50}$ (μM) |
|---|---|---|---|
| 1 | Cycloguanil | 8.148 ± 4.133 | |
| 2 | 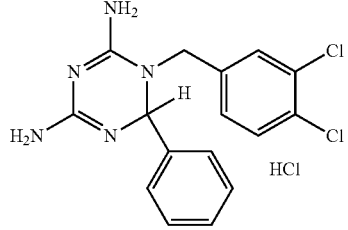 [SMILES: NC1=NC(c2ccccc2)N(Cc2ccc(Cl)c(Cl)c2)C(N)=N1 ; Cl] | 4.318 ± 1.188 | ND |
| 3 | 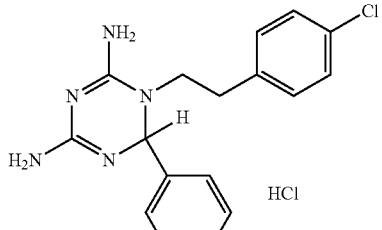 | 7.161 ± 0.626 | ND |

TABLE 1-continued
| No. | Compound | Antimalarial activity (FCR-3) Mean IC$_{50}$ (μM) | Cytotox SRB (HeLa) IC$_{50}$ (μM) |
|---|---|---|---|
| 4 | 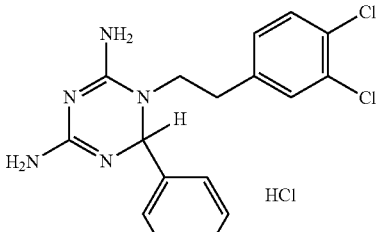 HCl | 4.766 ± 0.297 | ND |
| 5 | 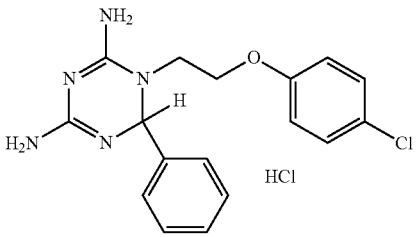 [SMILES: NC1=NC(c2ccccc2)N(CCOc2ccc(Cl)cc2)C(N)=N1 ; Cl] HCl | 4.833 ± 0.689 | ND |
| 6 | 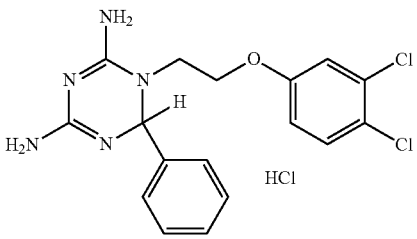 [SMILES: NC1=NC(c2ccccc2)N(CCOc2ccc(Cl)c(Cl)c2)C(N)=N1 ; Cl] HCl | 2.123 ± 0.750 | ND |
| 7 | 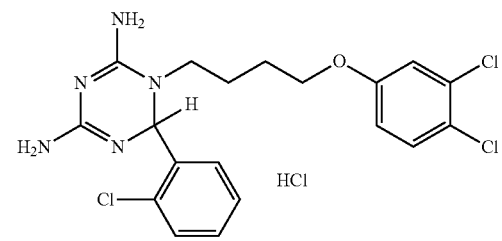 [SMILES: NC1=NC(c2ccccc2Cl)N(CCCCOc2ccc(Cl)c(Cl)c2)C(N)=N1 ; Cl] HCl | 2.570 ± 0.700 | ND |
| 8 | 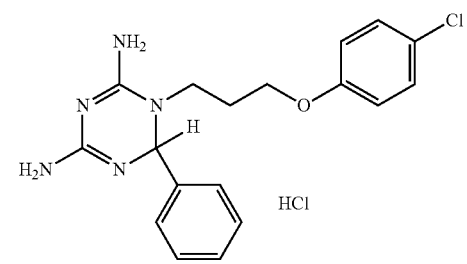 [SMILES: NC1=NC(c2ccccc2)N(CCCOc2ccc(Cl)cc2)C(N)=N1 ; Cl] HCl | 0.055 ± 0.010 | 39.0 |
| 9 | 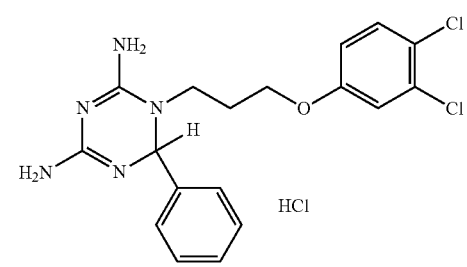 [SMILES: NC1=NC(c2ccccc2)N(CCCOc2ccc(Cl)c(Cl)c2)C(N)=N1 ; Cl] HCl | 0.0398 ± 0.010 | 33.5 |

TABLE 1-continued
| No. | Compound | Antimalarial activity (FCR-3) Mean IC$_{50}$ (μM) | Cytotox SRB (HeLa) IC$_{50}$ (μM) |
|---|---|---|---|
| 10 | 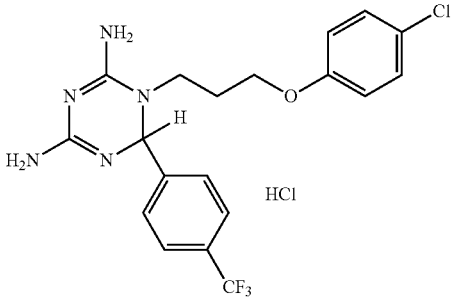 [SMILES: NC1=NC(c2ccc(C(F)(F)F)cc2)N(CCCOc2ccc(Cl)cc2)C(N)=N1 ; Cl] | 3.369 ± 0.168 | 11.0 |
| 11 | 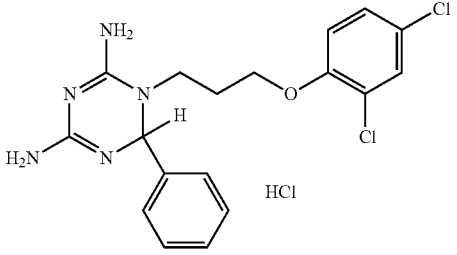 [SMILES: NC1=NC(c2ccccc2)N(CCCOc2ccc(Cl)cc2Cl)C(N)=N1 ; Cl] | 0.0001513 ± 0.000079 | 32.6 |
| 12 | 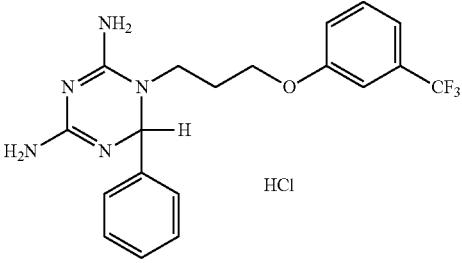 [SMILES: NC1=NC(c2ccccc2)N(CCCOc2cccc(C(F)(F)F)c2)C(N)=N1 ; Cl] | 0.0307 ± 0.0102 | 14.2 |
| 13 | 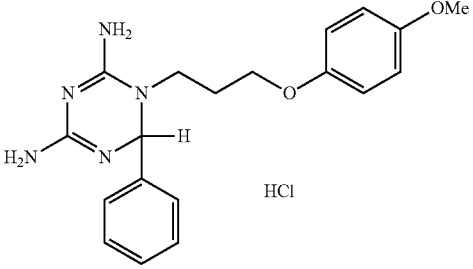 [SMILES: COc1ccc(OCCCN2C(N)=NC(N)=NC2c2ccccc2)cc1 ; Cl] | 0.0603 ± 0.0087 | 253.1 |
| 14 | 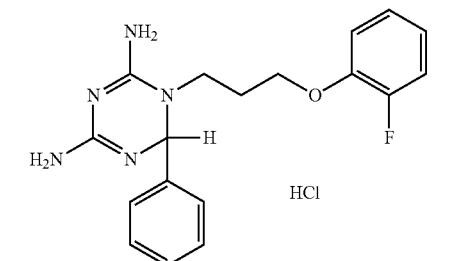 | 0.525 ± 0.0762 | 67.6 |

TABLE 1-continued
| No. | Compound | Antimalarial activity (FCR-3) Mean IC$_{50}$ (μM) | Cytotox SRB (HeLa) IC$_{50}$ (μM) |
|---|---|---|---|
| 15 | 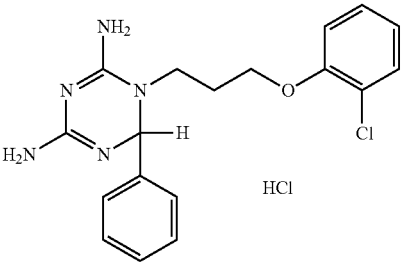 [SMILES: NC1=NC(c2ccccc2)N(CCCOc2ccccc2Cl)C(N)=N1 ; Cl] HCl | 0.1709 ± 0.0270 | 88.8 |
| 16 | 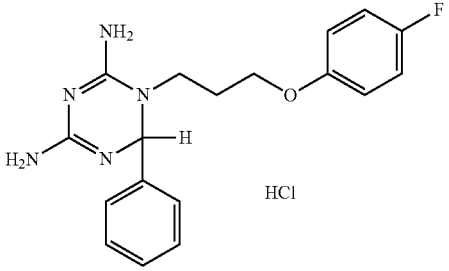 [SMILES: NC1=NC(c2ccccc2)N(CCCOc2ccc(F)cc2)C(N)=N1 ; Cl] HCl | 0.3953 ± 0.1092 | ND |
| 17 | 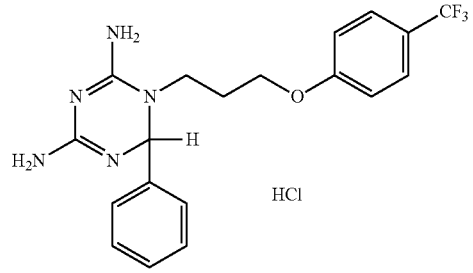 [SMILES: NC1=NC(c2ccccc2)N(CCCOc2ccc(C(F)(F)F)cc2)C(N)=N1 ; Cl] HCl | 0.0444 ± 0.0068 | ND |
| 18 | 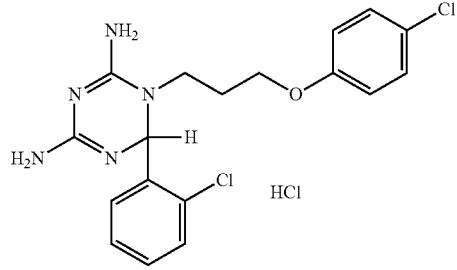 [SMILES: NC1=NC(c2ccccc2Cl)N(CCCOc2ccc(Cl)cc2)C(N)=N1 ; Cl] HCl | 0.859 0.606 | 15.7 |
| 19 | 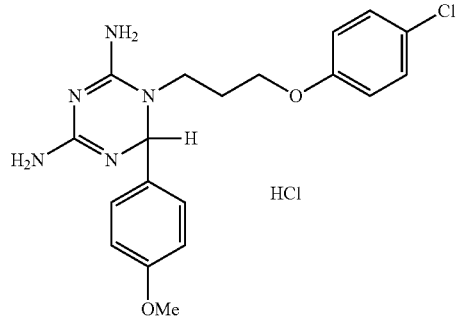 [SMILES: COc1ccc(C2N=C(N)N=C(N)N2CCCOc2ccc(Cl)cc2)cc1 ; Cl] HCl | 0.046 ± 0.017 | 25.0 |

TABLE 1-continued
| No. | Compound | Antimalarial activity (FCR-3) Mean IC$_{50}$ (μM) | Cytotox SRB (HeLa) IC$_{50}$ (μM) |
|---|---|---|---|
| 20 | 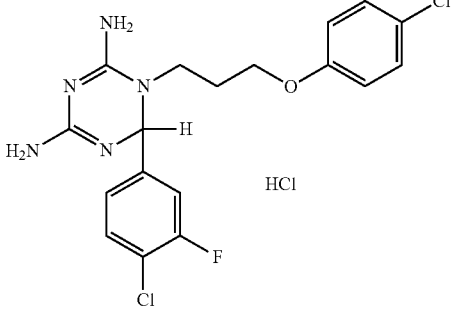 | 1.593 ± 0.000 | 13.7 |
| 21 | 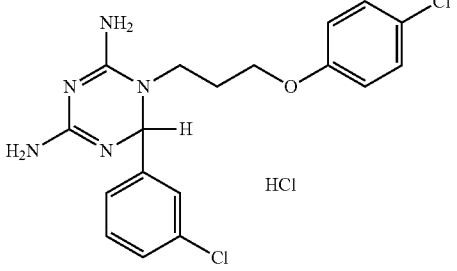 | 0.156 ± 0.012 | 14.1 |
| 22 | 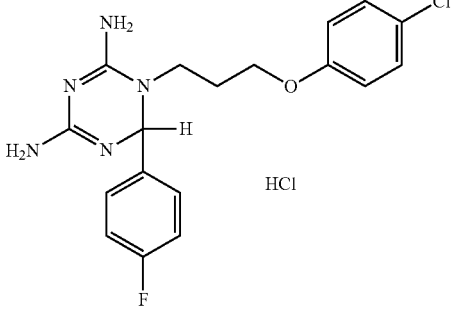 | 0.155 ± 0.048 | ND |
| 23 | 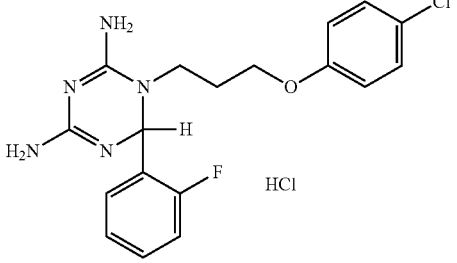 | 0.412 ± 0.080 | 52.2 |
| 24 | 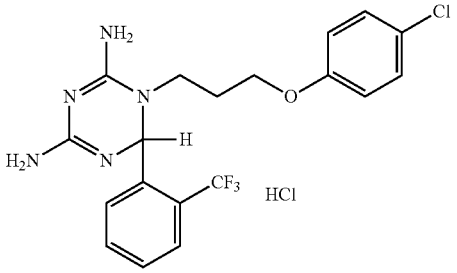 [SMILES: NC1=NC(c2ccccc2C(F)(F)F)N(CCCOc2ccc(Cl)cc2)C(N)=N1 ; Cl] | 3.237 ± 0.451 | 19.0 |

TABLE 1-continued
| No. | Compound | Antimalarial activity (FCR-3) Mean IC$_{50}$ (μM) | Cytotox SRB (HeLa) IC$_{50}$ (μM) |
|---|---|---|---|
| 25 | 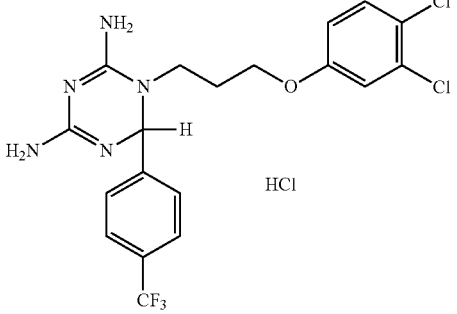 | 4.532 ± 0.631 | 13.1 |
| 26 | 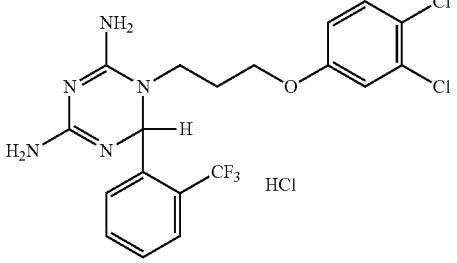 | 3.056 ± 0.042 | 11.8 |
| 27 | 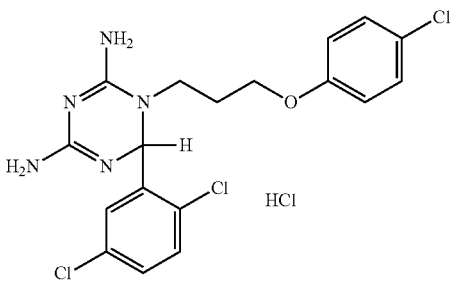 [SMILES: NC1=NC(c2cc(Cl)ccc2Cl)N(CCCOc2ccc(Cl)cc2)C(N)=N1 ; Cl] | 0.926 ± 0.128 | 10.9 |
| 28 | 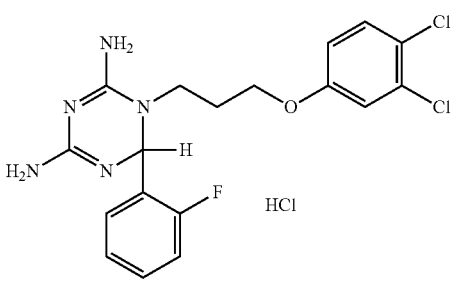 [SMILES: NC1=NC(c2ccccc2F)N(CCCOc2ccc(Cl)c(Cl)c2)C(N)=N1 ; Cl] | 0.337 ± 0.095 | 29.5 |
| 29 | 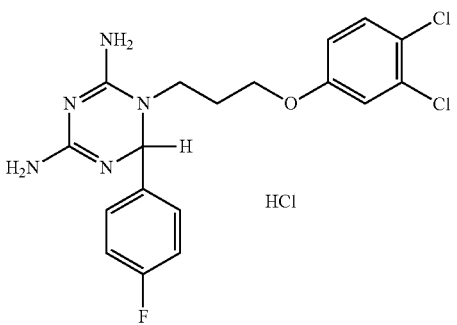 [SMILES: NC1=NC(c2ccc(F)cc2)N(CCCOc2ccc(Cl)c(Cl)c2)C(N)=N1 ; Cl] | 35.844 ± 8.974 | >200 14.6 |

TABLE 1-continued
| No. | Compound | Antimalarial activity (FCR-3) Mean IC$_{50}$ (μM) | Cytotox SRB (HeLa) IC$_{50}$ (μM) |
|---|---|---|---|
| 30 | 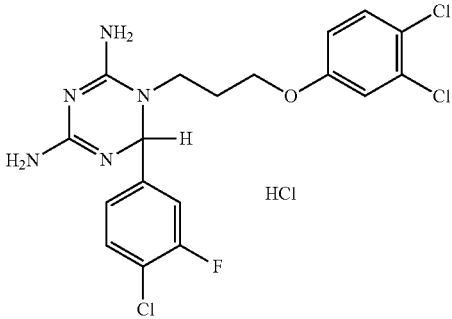 [SMILES: NC1=NC(c2ccc(Cl)c(F)c2)N(CCCOc2ccc(Cl)c(Cl)c2)C(N)=N1 ; Cl] HCl | 0.591 ± 0.077 | 14.5 |
| 31 | 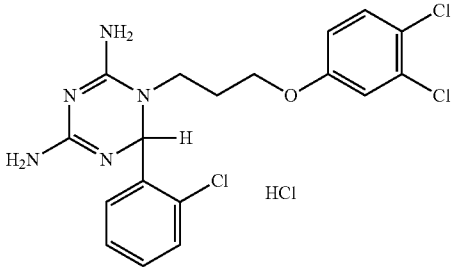 [SMILES: NC1=NC(c2ccccc2Cl)N(CCCOc2ccc(Cl)c(Cl)c2)C(N)=N1 ; Cl] HCl | 8.610 ± 0.998 | 13.7 |
| 32 | 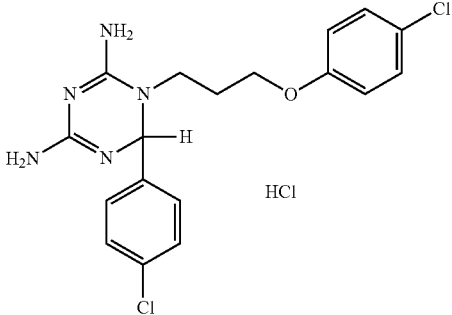 [SMILES: NC1=NC(c2ccc(Cl)cc2)N(CCCOc2ccc(Cl)cc2)C(N)=N1 ; Cl] HCl | 0.156 ± 0.129 | 15.6 |
| 33 | 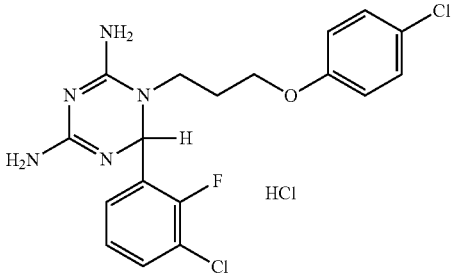 [SMILES: NC1=NC(c2cccc(Cl)c2F)N(CCCOc2ccc(Cl)cc2)C(N)=N1 ; Cl] HCl | 0.679 ± 0.221 | 23.0 |

TABLE 1-continued
| No. | Compound | Antimalarial activity (FCR-3) Mean IC$_{50}$ (μM) | Cytotox SRB (HeLa) IC$_{50}$ (μM) |
|---|---|---|---|
| 34 | 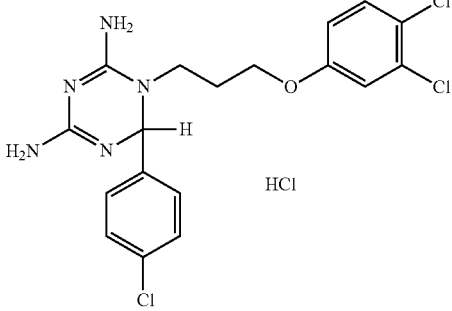 HCl | 0.061 ± 0.036 | 13.4 |
| 35 | 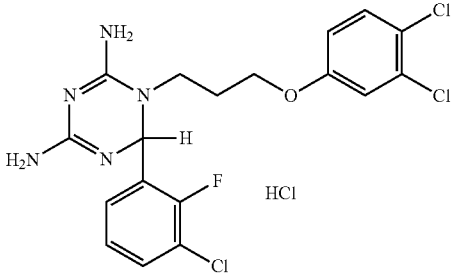 [SMILES: NC1=NC(c2cccc(Cl)c2F)N(CCCOc2ccc(Cl)c(Cl)c2)C(N)=N1 ; Cl] HCl | 0.098 ± 0.005 | 13.6 |
| 36 | 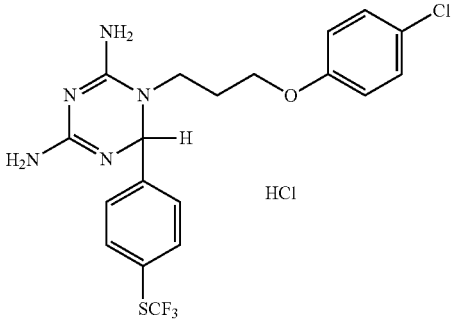 HCl | 2.390 ± 0.030 | ND |
| 37 | 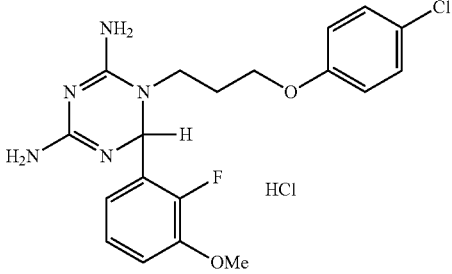 [SMILES: COc1cccc(C2N=C(N)N=C(N)N2CCCOc2ccc(Cl)cc2)c1F ; Cl] HCl | 0.077 ± 0.032 | 33.3 |

TABLE 1-continued
| No. | Compound | Antimalarial activity (FCR-3) Mean IC$_{50}$ (μM) | Cytotox SRB (HeLa) IC$_{50}$ (μM) |
|---|---|---|---|
| 38 | 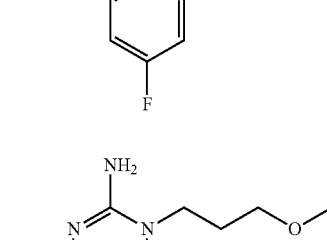 HCl | 0.163 ± 0.050 | 31.8 |
| 39 | 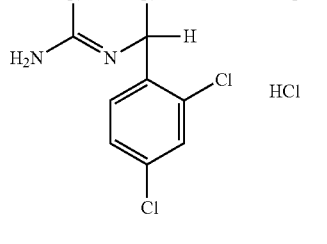 HCl | 2.511 ± 0.667 | 12.1 |
| 40 | 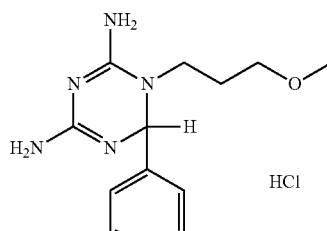 HCl | >50 | ND |
| 41 | 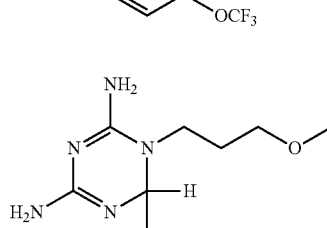 HCl | 0.050 ± 0.040 | ND |
| 42 | 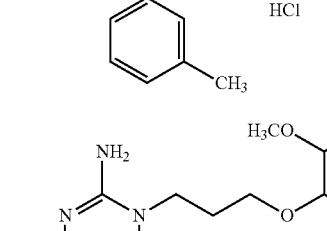 HCl | 0.047 ± 0.010 | ND |

TABLE 1-continued

| No. | Compound | Antimalarial activity (FCR-3) Mean IC$_{50}$ (μM) | Cytotox SRB (HeLa) IC$_{50}$ (μM) |
|---|---|---|---|
| 43 | 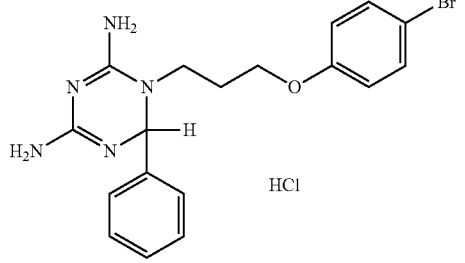 HCl | 0.024 ± 0.017 | ND |
| 44 | 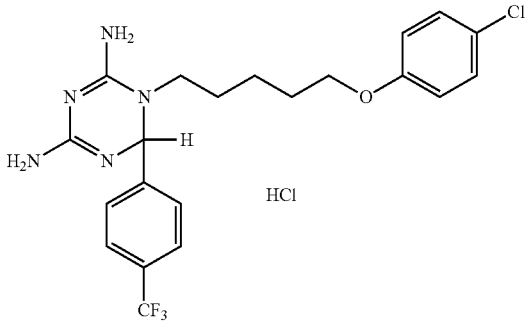 [SMILES: NC1=NC(c2ccc(C(F)(F)F)cc2)N(CCCCCOc2ccc(Cl)cc2)C(N)=N1 ; Cl] HCl | 3.980 ± 0.612 | ND |

*ND = Not done

An investigation into the in vivo properties of this class of compound has revealed that the compounds are poorly bioavailable as the hydrochloride salt, but that despite this poor bioavailability, they exhibit promising activity in the Peters 4-day suppressive test model, displaying a similar recrudescence pattern to chloroquine. The results are set out in Example 2.

Figure 2:
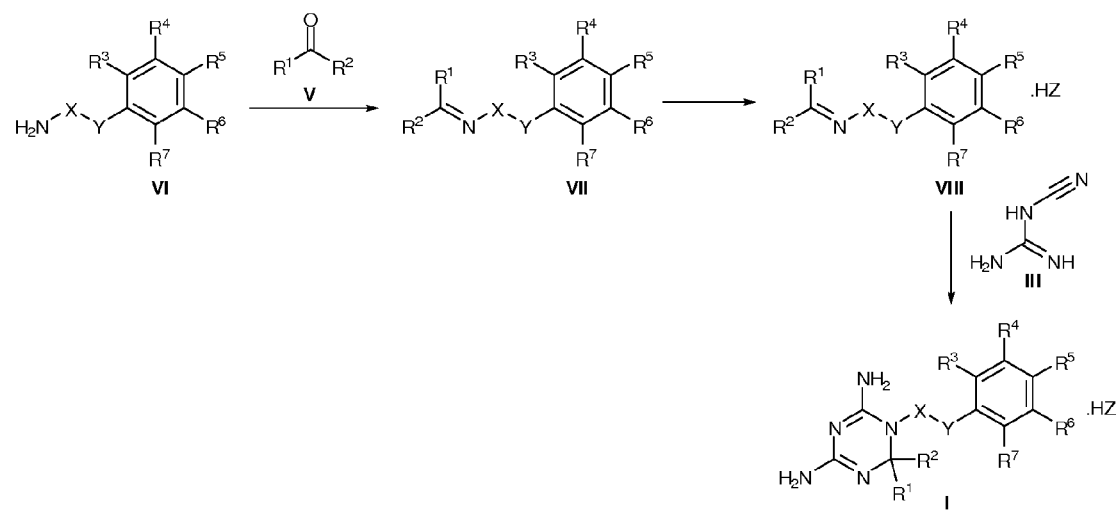

Two methods can be used for the synthesis of the compounds of the invention. The first involves the fusion of dicyandiamide III with the salt of the appropriate amine II at 150-170° C. (FIG. 1). The resulting biguanide salt IV is condensed with an aldehyde or ketone V in refluxing absolute ethanol in the presence of a small quantity of 32% hydrochloric acid to give the desired 1,2-dihydro-1,3,5-triazine-4,6-diamines I. The second approach involves the condensation of an appropriate amine VI with an aldehyde or ketone V in tetrahydrofuran containing anhydrous magnesium sulphate at ambient temperature to give the corresponding imine VII (FIG. 2). The formation of imine VII can also be achieved in the absence of solvent at elevated temperatures (100° C.) under vacuum. Compound VII is protonated with an acid in diethyl ether at ambient temperature to give the iminium salt VIII which is finally reacted with dicyandiamide III in N,N'-dimethylformamide at ambient temperature to give the desired 1,2-dihydro-1,3,5-triazine-4,6-diamines I.

Figure 3:
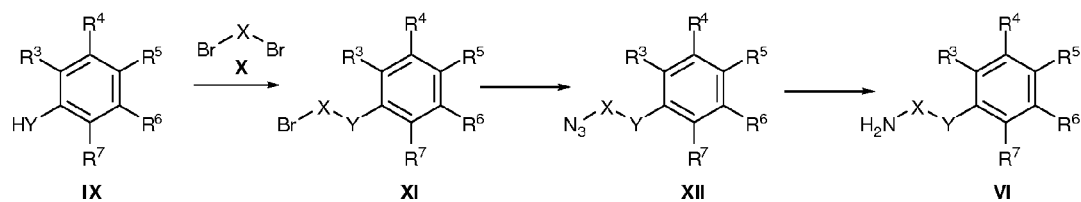

The required amines VI are prepared according to standard methods as detailed in FIG. 3. Alkylation of the appropriate phenol, thiophenol or aniline IX with the dibromoalkane of choice furnishes bromoalkane XI. Functional group interconversion of the bromide to the required amine VI is effected through the intermediacy of the corresponding azide XII.

In a modification of the first approach, the formation of the 1,2-dihydro-1,3,5-triazine-4,6-diamine I was achieved by the use of microwave radiation. It was found that, in most instances, the reaction time was substantially reduced. It was also found that, where production of the dihydrotriazine I could not be achieved using the approach depicted in FIG. 1, dihydrotriazine formation could be achieved by the use of microwave radiation. The microwave reactions were typically carried out at 85° C. and 100 W in 1,4-dioxane to facilitate dihydrotriazine formation. After 30 min the resulting solution containing the 1,2-dihydro-1,3,5-triazine-4,6-diamine I was allowed to cool to room temperature, and the desired product precipitated from this solution.

In a modification of the second approach, the formation of the imine VII was achieved by the use of microwave radiation. It was found that, in most instances, the reaction time was substantially reduced and the yield of the imine VII was increased. It was also found that, where production of imine VII could not be achieved using the approach depicted in FIG. 2, imine formation could be achieved by the use of microwave radiation. The microwave reactions were typically carried out at 100° C. and 150 W in 1,4-dioxane in the presence of Montmorillonite K-10 to facilitate imine formation. After 30 min the resulting solution containing the imine was allowed to cool to room temperature before drying (MgSO$_4$) and treating with HCl gas. Once saturated, the newly-formed iminium chloride is treated with dicyandiamide pre-dissolved in a minimum volume of DMF. The resulting mixture, still in the same tube, was then re-subjected to microwave irradiation using the same program parameters, namely T=100° C., P=150 W and T=30 min. Once the mixture had cooled to room temperature the reaction mixture was poured into a beaker containing diethyl ether. The desired product precipitated from this solution.

Thus, according to a fifth aspect of the invention, there is provided a method of preparing a compound of formula I,

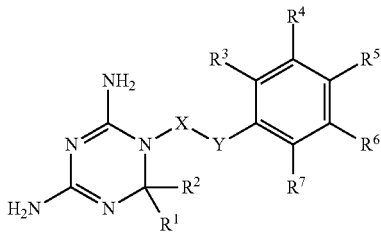

in which
R$^1$ and R$^2$ are independently selected from H, alkyl, aryl and heteroaryl, or R$^1$ and
R$^2$ together form a C$_5$-C$_7$ ring,
R$^3$-R$^7$ are independently selected from H, halogen, alkyl and alkoxy,
X is (CH$_2$)$_n$ in which n is 0-5,
Y is selected from CH$_2$, NR$^8$, O or S in which R$^8$ is H or alkyl,
salts thereof and stereoisomers thereof,
in which
"alkyl" means a group selected from
   C$_1$-C$_7$ straight chain alkyl groups, optionally substituted with one or more F, Cl, Br, O, S or N, and
   C$_1$-C$_7$ branched alkyl groups optionally substituted with one or more F, Cl, Br, O, S or N,
"aryl" means a group selected from
   phenyl, and
   phenyl substituted with one or more F, Cl, Br, S, N, C$_1$-C$_7$ alkoxy, nitrile, trifluoromethyl, C$_1$-C$_7$ straight chain alkyl groups and C$_1$-C$_7$ branched alkyl groups, the alkyl groups being optionally substituted with one or more F, Cl, Br, O, S or N,
"heteroaryl" means a group selected from thiophenyl, furyl, pyridinyl, isoxazolinyl, pyrrolinyl, oxazolinyl, thiazolinyl, imidazolyl which is optionally substituted with one or more F, Cl, Br, S, N, C$_1$-C$_7$ alkoxy, nitrile, trifluoromethyl, C$_1$-C$_7$ straight chain alkyl groups and C$_1$-C$_7$ branched alkyl groups, the alkyl groups being optionally substituted with one or more F, Cl, Br, O, S or N,
"halogen" means F, Cl or Br, and
"alkoxy" means a C$_1$-C$_7$ alkoxy group,
provided that:
(1) when R$^1$ and R$^2$ are both methyl, X is (CH$_2$)$_n$, n is 2-5 and Y is O, then R$^3$-R$^7$ are not all H,
(2) when R$^1$ and R$^2$ are independently selected from H, methyl, isopropyl, cyclohexyl, phenyl, 4-fluorophenyl, 4-chlorophenyl, 3,4-methylenedioxyphenyl, 4-acetamidophenyl, 4-methylthiophenyl or R$^1$ and R$^2$ together form —(CH$_2$)$_2$(CH(CH$_3$)—(CH$_2$)$_2$—, X is (CH$_2$)$_n$, n is 0-3 and Y is CH$_2$, then R$^3$-R$^7$ are not all H,
(3) when R$^1$ is selected from H, trifluoromethyl, undecyl, tert-butyl or phenyl and R$^2$ is H or methyl, when Y is CH$_2$ for X=(CH$_2$)$_n$ and n=0 and R$^5$ is H or chlorine, then R$^3$, R$^4$, R$^6$ and R$^7$ are not all H and when R$^4$ and R$^5$ are methoxy then not all of R$^3$, R$^6$ and R$^7$ are H, and
(4) when R$^1$ and R$^2$ are both methyl, X is (CH$_2$)$_n$, n is 0-3 and Y is CH$_2$, then neither R$^3$ nor R$^7$ is H,
the method including the steps of:
   reacting a compound of formula II with dicyandiamide III to produce a biguanide of formula IV; and
   condensing the biguanide of formula IV with an aldehyde or ketone of formula V to produce the compound of formula I.

The salt may be the salt of any pharmaceutically suitable acid such as hydrochloric acid, picric acid, nitric acid or acetic acid According to a sixth aspect of the invention, there is provided a method of preparing a compound of formula I,

in which
R$^1$ and R$^2$ are independently selected from H, alkyl, aryl and heteroaryl, or R$^1$ and R$^2$ together form a C$_5$-C$_7$ ring,
R$^3$-R$^7$ are independently selected from H, halogen, alkyl and alkoxy,
X is (CH$_2$)$_n$ in which n is 0-5,
Y is selected from CH$_2$, NR$^8$, O or S in which R$^8$ is H or alkyl,
salts thereof and stereoisomers thereof,
in which
"alkyl" means a group selected from
   C$_1$-C$_7$ straight chain alkyl groups, optionally substituted with one or more F, Cl, Br, O, S or N, and
   C$_1$-C$_7$ branched alkyl groups optionally substituted with one or more F, Cl, Br, O, S or N,
"aryl" means a group selected from
   phenyl, and
   phenyl substituted with one or more F, Cl, Br, S, N, C$_1$-C$_7$ alkoxy, nitrile, trifluoromethyl, C$_1$-C$_7$ straight chain alkyl groups and C$_1$-C$_7$ branched alkyl groups, the alkyl groups being optionally substituted with one or more F, Cl, Br, O, S or N,
"heteroaryl" means a group selected from thiophenyl, furyl, pyridinyl, isoxazolinyl, pyrrolinyl, oxazolinyl, thiazolinyl, imidazolyl which is optionally substituted with one or more F, Cl, Br, S, N, C$_1$-C$_7$ alkoxy, nitrile, trifluoromethyl, C$_1$-C$_7$ straight chain alkyl groups and C$_1$-C$_7$ branched alkyl groups, the alkyl groups being optionally substituted with one or more F, Cl, Br, O, S or N,
"halogen" means F, Cl or Br, and
"alkoxy" means a C$_1$-C$_7$ alkoxy group,
provided that:
(1) when R$^1$ and R$^2$ are both methyl, X is (CH$_2$)$_n$, n is 2-5 and Y is O, then R$^3$-R$^7$ are not all H,
(2) when R$^1$ and R$^2$ are independently selected from H, methyl, isopropyl, cyclohexyl, phenyl, 4-fluorophenyl, 4-chlorophenyl, 3,4-methylenedioxyphenyl, 4-acetamidophenyl, 4-methylthiophenyl or R$^1$ and R$^2$ together form —(CH$_2$)$_2$(CH(CH$_3$)—(CH$_2$)$_2$—, X is (CH$_2$)$_n$, n is 0-3 and Y is CH$_2$, then R$^3$-R$^7$ are not all H,
(3) when R$^1$ is selected from H, trifluoromethyl, undecyl, tert-butyl or phenyl and R$^2$ is H or methyl, Y is CH$_2$ for X=(CH$_2$)$_n$ and n=0 and R$^5$ is H or chlorine, then R$^3$, R$^4$, R$^6$ and R$^7$ are not all H and when R$^4$ and R$^5$ are methoxy then not all of R$^3$, R$^6$ and R$^7$ are H, and
(4) when R$^1$ and R$^2$ are both methyl, X is (CH$_2$)$_n$, n is 0-3 and Y is CH$_2$, then neither R$^3$ nor R$^7$ is H.

the method including the steps of:
condensing an amine of formula VI with an aldehyde or ketone of formula V to produce an imine of formula VII;
converting the imine of formula VII to the iminium salt VIII; and
reacting the iminium salt of formula VIII with dicyandiamide III to produce the compound of formula I.

The condensation step to produce the imine of formula VII may be conducted using microwave energy.

According to a seventh aspect of the invention, there is provided the use of a compound of formula I

Figure 4:
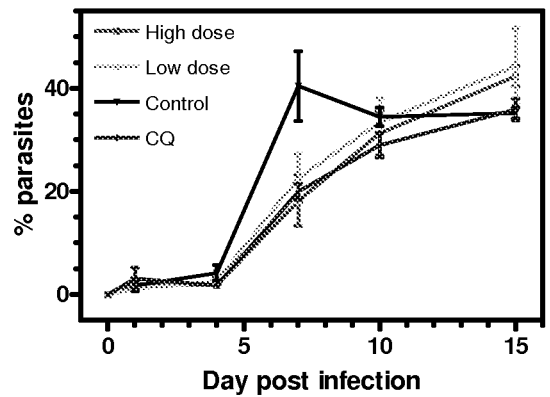
Figure 5:
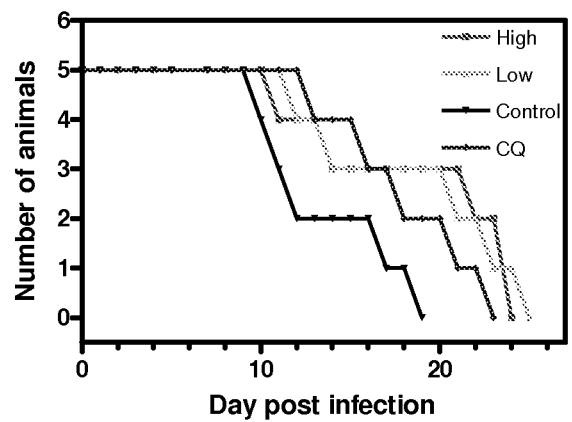

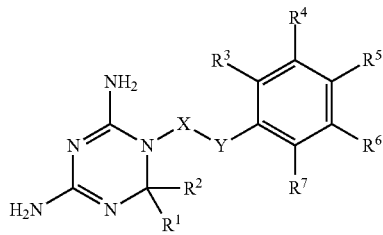

in which
R$^1$ and R$^2$ are independently selected from H, alkyl, aryl and heteroaryl, or R$^1$ and R$^2$ together form a C$_5$-C$_7$ ring,
R$^3$-R$^7$ are independently selected from H, halogen, alkyl and alkoxy,
X is (CH$_2$)$_n$ in which n is 0-5,
Y is selected from CH$_2$, NR$^8$, O or S in which R$^8$ is H or alkyl,
salts thereof and stereoisomers thereof,
in which
"alkyl" means a group selected from
  C$_1$-C$_7$ straight chain alkyl groups, optionally substituted with one or more F, Cl, Br, O, S or N, and
  C$_1$-C$_7$ branched alkyl groups optionally substituted with one or more F, Cl, Br, O, S or N,
"aryl" means a group selected from
  phenyl, and
  phenyl substituted with one or more F, Cl, Br, S, N, C$_1$-C$_7$ alkoxy, nitrile, trifluoromethyl, C$_1$-C$_7$ straight chain alkyl groups and C$_1$-C$_7$ branched alkyl groups, the alkyl groups being optionally substituted with one or more F, Cl, Br, O, S or N,
"heteroaryl" means a group selected from thiophenyl, furyl, pyridinyl, isoxazolinyl, pyrrolinyl, oxazolinyl, thiazolinyl, imidazolyl which is optionally substituted with one or more F, Cl, Br, S, N, C$_1$-C$_7$ alkoxy, nitrile, trifluoromethyl, C$_1$-C$_7$ straight chain alkyl groups and C$_1$-C$_7$ branched alkyl groups, the alkyl groups being optionally substituted with one or more F, Cl, Br, O, S or N,
"halogen" means F, Cl or Br, and
"alkoxy" means a C$_1$-C$_7$ alkoxy group,
provided that:
(1) when R$^1$ and R$^2$ are both methyl, X is (CH$_2$)$_n$, n is 2-5 and Y is O, then R$^3$-R$^7$ are not all H,
(2) when R$^1$ and R$^2$ are independently selected from H, methyl, isopropyl, cyclohexyl, phenyl, 4-fluorophenyl, 4-chlorophenyl, 3,4-methylenedioxyphenyl, 4-acetamidophenyl, 4-methylthiophenyl or R$^1$ and R$^2$ together form —(CH$_2$)$_2$(CH(CH$_3$)—(CH$_2$)$_2$—, X is (CH$_2$)$_n$, n is 0-3 and Y is CH$_2$, then R$^3$-R$^7$ are not all H, in the manufacture of a medicament for substantially inhibiting dihydrofolate reductase enzymes, or for the treatment or prophylaxis of malaria resistant to antifolate compounds including cycloguanil and pyrimethamine, The invention is now described, by way of example, with reference to the following Examples and the Figures in which
FIGS. 1-3 are reaction schemes;
FIG. 4 shows inherent antimalarial activity of compound AL 419-11; and
FIG. 5 shows survival times of infected mice during the treatment and evaluation with AL 419-11.

EXAMPLE 1

Preparation of 4,6-diamino-1,2-dihydro-1,3,5-triazines of Formula I

Three methods were employed for the preparation of 1,2-dihydro-1,3,5-triazine-4,6-diamines of the general formula I.
Method A (FIG. 1)
3-(4-(trifluoromethyl)phenoxy)propyl-1-amine hydrochloride (214 mg, 0.839 mmol) and dicyandiamide (84.7 mg, 0.839 mmol) were ground and intimately mixed. The mixture was slowly heated in an oil bath with stirring to 140° C. over a period of 30 minutes. The reaction mixture was then cooled.[12]

To a solution of N'-[3-(4-trifluoromethylphenoxy)propyl] biguanide hydrochloride (0.839 mmol) in dioxane (2 ml) in a microwave tube was added benzaldehyde (5 eq., 4.19 mmol, 0.43 ml) and conc. HCl (1 drop). The contents were irradiated with microwave energy (power=100 W, temperature=85° C., time=30 min). After cooling to ambient temperature, the product precipitated from the reaction mixture and was collected by filtration and washed with diethyl ether. This gave 90.1 mg (25%) of 6-phenyl-1-(3-(4-(trifluoromethyl)phenoxy)propyl)-1,6-dihydro-1,3,5-triazine-2,4-diamine hydrochloride; δ$_H$ (400 MHz, CD$_3$OD) 7.62 (2H, d, J 8.5), 7.53-7.36 (5H, m), 7.09 (2H, d, J 8.5), 5.80 (1H, s), 4.20-4.07 (2H, m), 3.85-3.71 (1H, m), 3.44-3.36 (1H, m), 2.30-1.95 (2H, m); HRMS (ESI): m/z 392.1698 (M+H)$^+$; calc. For C$_{19}$H$_{21}$F$_3$N$_5$O: 392.1698.
Method B (FIG. 2)
3-(4-Chlorophenoxy)propan-1-amine (836 mg, 4.50 mmol) and benzaldehyde (1.3 eq., 5.9 mmol, 0.59 ml) were dissolved in dry ether in a nitrogen-purged oven-dried flask. Activated 4 Å molecular sieves (about 10) and Montmorillonite K-10 (spatula-full) were added and the resulting heterogeneous mixture heated under reflux for 3 h. The mixture was allowed to cool to RT and was then filtered into an oven-dried nitrogen-purged flask. The solids were washed with additional anhydrous ether. Hydrogen chloride gas was gently bubbled through this solution until saturation was reached. A white precipitate formed. The resulting suspension was subjected to vacuum and the ether and excess HCl evaporated in vacuo. The flask was re-purged with nitrogen. Dicyandiamide and anhydrous N,N'-dimethylformamide were added and the resulting mixture stirred under nitrogen overnight (20 h). The reaction mixture was poured into ether:acetone (9:1) (300 ml) and stirred until a solid had formed at the bottom of the flask. The solid was filtered and washed with ether. The crude product was purified by reverse-phase MPLC (Biotage) using MeOH:H$_2$O mixture gradient elution. 1-(3-(4-Chlorophenoxy)propyl)-6-phenyl-1,2-dihydro-1,3,5-triazine-4,6-diamine hydrochloride was obtained as a white solid (223 mg, 0.567 mmol, 13%). δ$_H$ (400 MHz, CD$_3$OD) 7.53-7.45 (3H, m), 7.41 (2H, dd, J 2.4, 7.3), 7.29 (2H, d, J 9.1), 6.93 (2H, d, J 9.1), 5.76 (1H, s), 4.12-3.98 (2H, m), 3.79-3.70 (1H, m), 3.42-3.35 (1H, m), 2.24-1.95 (2H, m); δ$_C$ (101 MHz, CD$_3$OD) 160.12, 159.63, 159.51, 141.06, 131.83, 131.31, 131.26, 128.25, 127.76, 117.88, 70.84, 66.98, 46.46, 28.49; HRMS (ESI): m/z 358.1405 (M+H)$^+$; calc. For C$_{18}$H$_{21}$ClN$_5$O: 358.1435

Method C (FIG. 2)

Montmorillonite K1-10 (29 mg) was added to a microwave tube containing a solution of 4-(3,4-dichlorophenoxy)butan-1-amine (87 mg, 0.372 mmol) and 2-chlorobenzaldehyde (3 eq., 1.12 mmol, 126 μl) in 1,4-dioxane (2 ml). The contents were irradiated with microwave energy (power=150 W, temperature=100° C., time=30 min). The mixture was allowed to cool to ambient temperature, dried with MgSO$_4$. Hydrogen chloride gas was bubbled through the mixture until saturation. Dicyandiamide (1.2 eq., 0.45 mmol, 38 mg) dissolved in a minimum volume of anhydrous DMF was added to the above mixture. The tube was inserted in the microwave synthesiser and was irradiated with microwave energy (power=150 W, temperature=100° C., time=30 min). After cooling to ambient temperature the contents were poured into diethyl ether. The resulting suspension was then filtered through Celite. The solids were washed copiously with diethyl ether. Thereafter methanol was used to elute the product 6-(2-chlorophenyl)-1-(4-(3,4-dichlorophenoxy)butyl)-1,6-dihydro-1,3,5-triazine-2,4-diamine, (108 mg, 0.227 mmol, 61%); HRMS (ESI): m/z 440.0814 (M+H)$^+$; calc. for C$_{19}$H$_{21}$Cl$_3$N$_5$O: 440.0812

Method D (FIG. 2)

3-(2-Chlorophenoxy)propyl-1-amine (270.6 mg, 1.457 mmol) and benzaldehyde (1.2 eq., 1.75 mmol, 178 μl) were stirred together under vacuum at 100° C. for 2 hours. The resulting imine mixture was cooled, treated with 1,4-dioxane (2 ml) and stirred on molecular sieves for 30 min. After removal of the molecular sieves, the mixture was treated with hydrogen chloride gas followed by dicyandiamide (1.2 eq., 1.75 mmol, 147 mg) dissolved in a minimum of N,N'-dimethyl formamide. The contents were irradiated with microwave energy (power=150 W, temperature=100° C., time=1 hour). The mixture was allowed to cool to ambient temperature and the desired product precipitated from solution. The solids were filtered off and washed with diethyl ether to afford 1-(3-(2-chlorophenoxy)propyl)-6-phenyl-1,6-dihydro-1,3,5-triazine-2,4-diamine hydrochloride (273.3 mg, 48%). $\delta_H$ (400 MHz, CD$_3$OD) 7.55-7.38 (6H, m), 7.30 (1H, tdd, J 0.8, 1.6, 7.4), 7.10 (1H, d, J 8.3), 7.01-6.94 (1H, m), 5.79 (1H, s), 4.23-4.09 (2H, m), 3.78-3.65 (1H, m), 3.46 (1H, dt, J 7.6, 15.3), 2.28-2.15 (1H, m), 2.11-1.99 (1H, m); $\delta_C$ (101 MHz, CD$_3$OD) 160.02, 159.59, 156.04, 141.17, 132.09, 131.89, 131.35, 130.12, 128.29, 124.43, 123.76, 115.44, 71.20, 67.26, 46.20, 28.46; HRMS (ESI): m/z 358.1391 (M+H)$^+$; calc. For C$_{18}$H$_{21}$ClN$_6$O: 358.1435

Method E (FIG. 2)

3-(4-Chlorophenoxy)propyl-1-amine (234.4 mg, 1.267 mmol) and α,α,α,-trifluoro-p-tolualdehyde (1.2 eq., 1.52 mmol, 203 μl) were stirred together under vacuum at 25-100° C. for 1 hour. The resulting imine mixture was cooled, treated with 1,4-dioxane (2 ml) and stirred on molecular sieves for 1.5 h. After removal of the molecular sieves, the mixture was treated with hydrogen chloride gas followed by dicyandiamide (1.2 eq., 1.52 mmol, 128 mg) dissolved in a minimum of N,N'-dimethyl formamide. Dicyandiamide and anhydrous N,N'-dimethyl formamide were added and the resulting mixture stirred under nitrogen at 100° C. overnight (20 h). A precipitate forms, which was washed with acetone, and recrystallized from methanol to afford 275.1 mg of 1-(3-(4-chlorophenoxy)propyl)-6-(4-(trifluoromethyl)phenyl)-1,6-dihydro-1,3,5-triazine-2,4-diamine hydrochloride. $\delta_H$ (400 MHz, DMSO-d$_6$) 7.88 (2H, d, J 8.2), 7.59 (2H, d, J 8.2), 7.36 (2H, d, J 8.9), 6.98 (2H, d, J 8.9), 5.98 (1H, s), 4.10-3.99 (2H, m), 3.90-3.78 (1H, m), 3.29-3.21 (1H, m), 2.14-1.82 (2H, m); $\delta_H$ (400 MHz, CD$_3$OD) 7.80 (2H, d, J 8.1), 7.61 (2H, d, J 8.3), 7.32-7.26 (2H, m), 6.97-6.91 (2H, m), 5.91 (1H, s), 4.14-4.02 (2H, m), 3.89-3.78 (1H, m), 3.39 (1H, dt, J 7.2, 14.6), 2.28-2.13 (1H, m), 2.13-2.00 (1H, m); $\delta_C$ (101 MHz, CD$_3$OD) 160.13, 159.63, 159.50, 145.39, 133.61 (1C, q, J$_{C-F}$ 32.5), 131.28, 128.95, 128.26 (2C, q, J$_{C-F}$ 3.8), 127.75, 126.14 (1C, q, J$_{C-F}$ 271.5), 117.82, 69.98, 66.89, 46.89, 28.56; HRMS (ESI): m/z 426.1302 (M+H)$^+$; calc. For C$_{19}$H$_{20}$ClF$_3$N$_5$O: 426.1308

The following compounds were prepared using these methods:

1-(3,4-Dichlorobenzyl)-6-phenyl-1,6-dihydro-1,3,5-triazine-2,4-diamine hydrochloride. $\delta_H$ (400 MHz, CD$_3$OD) 7.55 (1H, d, J 8.3), 7.48-7.42 (3H, m), 7.42-7.35 (3H, m), 7.21 (1H, dd, J 2.1, 8.3), 5.75 (1H, s), 4.83 (1H, d, J 17.2), 4.41 (1H, d, J 17.2); $\delta_C$ (101 MHz, CD$_3$OD) 160.46, 159.83, 140.47, 137.57, 134.64, 133.79, 132.91, 131.92, 131.28, 131.08, 128.80, 128.38, 70.68, 51.29; HRMS (ESI): m/z 348.0792 (M+H)$^+$; calc. For C$_{16}$H$_{16}$Cl$_2$N$_5$: 348.0783

1-(4-Chlorophenethyl)-6-phenyl-1,6-dihydro-1,3,5-triazine-2,4-diamine hydrochloride. $\delta_H$ (400 MHz, DMSO-d$_6$) 8.78 (1H, s), 7.74 (2H, s), 7.52-7.20 (9H, m), 5.81 (1H, s), 3.89 (1H, ddd, J 6.1, 9.1, 14.9), 3.19 (1H, ddd, J 5.8, 9.4, 15.0), 3.02-2.84 (1H, m), 2.82-2.68 (1H, m); $\delta_C$ (101 MHz, DMSO-d$_6$) 157.12, 156.91, 139.54, 136.74, 131.12, 130.89, 130.56, 129.17, 129.00, 128.41, 128.14, 125.93, 66.74, 47.92, 31.82; HRMS (ESI): m/z 328.1330 (M+H)$^+$; calc. For C$_{17}$H$_{19}$ClN$_5$: 328.1329

1-(3,4-Dichlorophenethyl)-6-phenyl-1,6-dihydro-1,3,5-triazine-2,4-diamine hydrochloride. HRMS (ESI): m/z 362.0943 (M+H)$^+$; calc. For C$_{17}$H$_{18}$Cl$_2$N$_5$: 362.0939

1-(2-(4-Chlorophenoxy)ethyl)-6-phenyl-1,6-dihydro-1,3,5-triazine-2,4-diamine hydrochloride. $\delta_H$ (400 MHz, CD$_3$OD) 7.43 (5H, s), 7.28 (2H, d, J 9.1), 6.88 (2H, d, J 9.0), 5.93 (1H, s), 4.17-4.10 (1H, m), 4.10-4.03 (1H, m), 3.94 (1H, ddd, J 3.5, 4.8, 15.9), 3.74 (1H, ddd, J 3.9, 7.9, 16.0); $\delta_C$ (50 MHz, CD$_3$OD) 160.64, 159.57, 159.14, 141.12, 131.70, 131.23, 130.62, 128.16, 127.85, 117.89, 71.41, 67.72, 63.80; HRMS (ESI): m/z 344.1287 (M+H)$^+$; calc. For C$_{17}$H$_{19}$ClN$_5$O: 344.1278

1-(2-(3,4-Dichlorophenoxy)ethyl)-6-phenyl-1,6-dihydro-1,3,5-triazine-2,4-diamine hydrochloride. $\delta_H$ (400 MHz, CD$_3$OD) 7.43 (5H, s), 7.42 (1H, d, J 9.3), 7.06 (1H, d, J 2.9), 6.85 (1H, dd, J 2.9, 8.9), 5.92 (1H, s), 4.15 (1H, ddd, J 3.9, 5.0, 10.1), 4.11-4.03 (1H, m), 3.95 (1H, ddd, J 3.4, 5.0, 16.0), 3.75 (1H, ddd, J 3.8, 7.8, 16.0); $\delta_C$ (101 MHz, CD$_3$OD) 160.63, 159.71, 159.55, 141.29, 134.61, 132.85, 131.69, 131.26, 128.13, 126.25, 118.43, 116.63, 71.28, 67.93, 49.13; HRMS (ESI): m/z 378.0883 (M+H)$^+$; calc. For C$_{17}$H$_{18}$Cl$_2$N$_5$O: 378.0888

1-(3-(3,4-Dichlorophenoxy)propyl)-6-phenyl-1,6-dihydro-1,3,5-triazine-2,4-diamine hydrochloride. $\delta_H$ (400 MHz, CD$_3$OD) 7.52-7.46 (3H, m), 7.45 (1H, br s), 7.44-7.39 (2H, m), 7.13 (1H, d, J 2.9), 6.91 (1H, dd, J 2.9, 8.9), 5.78 (1H, s), 4.19-3.93 (2H, m), 3.74 (1H, ddd, J 6.0, 7.7, 15.3), 3.46-3.23 (1H, m), 2.22-2.10 (1H, m), 2.09-1.96 (1H, m); $\delta_C$ (101 MHz, CD$_3$OD) 160.08 (2C), 159.60, 141.11, 134.64, 132.87, 131.84, 131.31, 128.24, 125.84, 118.33, 116.74, 70.77, 67.34, 46.38, 28.31; HRMS (ESI): m/z 392.1065 (M+H)$^+$; calc. for C$_{18}$H$_{20}$Cl$_2$N$_5$O: 392.1045

1-(3-(2,4-Dichlorophenoxy)propyl)-6-phenyl-1,6-dihydro-1,3,5-triazine-2,4-diamine hydrochloride. $\delta_H$ (400 MHz, CD$_3$OD) 7.54-7.38 (6H, m), 7.30 (1H, dd, J 2.6, 8.8), 7.07 (1H, d, J 8.9), 5.77 (1H, s), 4.14 (2H, dt, J 4.6, 6.1), 3.70 (1H, ddd, J 5.3, 8.0, 15.5), 3.45 (1H, dd, J 7.8, 15.4), 2.27-2.14 (1H, m), 2.10-1.98 (1H, m); δ$_C$ (101 MHz, CD$_3$OD) 160.06, 159.59, 155.06, 141.12, 131.93, 131.65, 131.36, 129.96, 128.31, 127.94, 125.33, 116.37, 71.21, 67.80, 46.18, 28.33; HRMS (ESI): m/z 392.1059 (M+H)$^+$; calc. for C$_{18}$H$_{20}$Cl$_2$N$_5$O: 392.1045

6-Phenyl-1-(3-(3-(trifluoromethyl)phenoxy)propyl)-1,6-dihydro-1,3,5-triazine-2,4-diamine hydrochloride. HRMS (ESI): m/z 392.1698 (M+H)$^+$; calc. for C$_{19}$H$_{21}$F$_3$N$_5$O: 392.1698

1-(3-(4-Methoxyphenoxy)propyl)-6-phenyl-1,6-dihydro-1,3,5-triazine-2,4-diamine hydrochloride. δ$_H$ (400 MHz, CD$_3$OD) 7.49 (2H, dd, J 1.9, 5.3), 7.41 (2H, dd, J 2.4, 7.2), 6.96-6.78 (5H, m), 5.75 (1H, s), 4.04-3.97 (2H, m), 3.76 (3H, s), 3.74-3.65 (1H, m), 3.41-3.37 (1H, m), 2.15-2.06 (1H, m), 2.06-1.93 (1H, m); δ$_C$ (101 MHz, CD$_3$OD) 156.47, 156.20, 155.35, 154.75, 141.20, 131.86, 131.35, 128.21, 117.35, 116.47, 70.91, 67.10, 56.91, 46.39, 28.66; HRMS (ESI): m/z 354.1911 (M+H)$^+$; calc. for C$_{19}$H$_{24}$N$_5$O$_2$: 354.1930

1-(3-(2-Fluorophenoxy)propyl)-6-phenyl-1,3,5-triazine-2,4-diamine hydrochloride. HRMS (ESI): m/z 342.1728 (M+H)$^+$; calc. for C$_{18}$H$_{21}$FN$_5$O: 342.1730

1-(3-(4-Fluorophenoxy)propyl)-6-phenyl-1,6-dihydro-1,3,5-triazine-2,4-diamine hydrochloride. δ$_H$ (400 MHz, CD$_3$OD) 7.57-7.35 (5H, m), 7.11-6.85 (4H, m), 5.78 (1H, s), 4.10-3.94 (2H, m), 3.75 (1H, ddd, J 5.8, 7.6, 15.3), 3.45-3.34 (1H, m), 2.25-1.90 (2H, m); δ$_C$ (101 MHz, CD$_3$OD) 160.09, 159.66 (1C, d, J$_{C-F}$ 237.0), 159.61, 157.00 (1C, d, J$_{C-F}$ 2.2), 141.16, 131.85, 131.33, 128.23, 117.64 (2C, d, J$_{C-F}$ 21.5), 117.49 (2C, d, J$_{C-F}$ 6.1), 70.84, 67.08, 46.41, 28.57; HRMS (ESI): m/z 342.1734 (M+H)$^+$; calc. for C$_{18}$H$_{21}$FN$_5$O: 342.1730

1-(3-(4-Chlorophenoxy)propyl)-6-(2-chlorophenyl)-1,6-dihydro-1,3,5-triazine-2,4-diamine hydrochloride. δ$_H$ (400 MHz, CD$_3$OD) 7.62-7.35 (4H, m), 7.33-7.24 (2H, m), 6.97-6.89 (2H, m), 6.20 (1H, s), 4.22-3.94 (2H, m), 3.85-3.71 (1H, m), 3.32-3.25 (1H, m), 2.28-2.12 (1H, m), 2.11-1.96 (1H, m); δ$_C$ (101 MHz, CD$_3$OD) 160.25, 159.48, 159.43, 137.67, 134.64, 133.36, 132.66, 131.27, 130.13, 129.55, 127.76, 117.80, 68.26, 66.70, 46.49, 28.37; HRMS (ESI): m/z 392.1016 (M+H)$^+$; calc. for C$_{18}$H$_{20}$Cl$_2$N$_5$O: 392.1045

1-(3-(4-Chlorophenoxy)propyl)-6-(4-methoxyphenyl)-1,6-dihydro-1,3,5-triazine-2,4-diamine hydrochloride. δ$_H$ (400 MHz, CD$_3$OD) 7.38 (2H, d, J 8.8), 7.31 (2H, d, J 9.0), 7.03 (2H, d, J 8.7), 6.94 (2H, d, J 9.0), 5.74 (1H, s), 4.13-3.98 (2H, m), 3.86 (3H, s), 3.76-3.61 (1H, m), 3.47-3.24 (1H, m), 2.24-2.08 (1H, m), 2.02 (1H, tt, J 6.6, 13.1); δ$_C$ (101 MHz, CD$_3$OD) 163.23, 160.03, 159.59, 159.47, 132.85, 131.25, 129.85, 127.72, 117.88, 116.55, 70.67, 66.96, 56.77, 46.13, 28.44; HRMS (ESI): m/z 388.1541 (M+H)$^+$; calc. for C$_{19}$H$_{23}$ClN$_5$O$_2$: 388.1540

6-(4-Chloro-3-fluorophenyl)-1-(3-(4-chlorophenoxy)propyl)-1,6-dihydro-1,3,5-triazine-2,4-diamine hydrochloride. δ$_H$ (400 MHz, CD$_3$OD) 7.86 (2H, dd, J 7.7, 14.7), 7.76-7.67 (2H, m), 7.51-7.41 (1H, m), 7.14-7.09 (1H, m), 7.03-6.85 (1H, m), 6.19 (1H, s), 4.26-4.01 (2H, m), 3.73 (1H, ddd, J 4.3, 6.0, 15.1), 3.31-3.17 (1H, m), 2.27-2.14 (1H, m), 2.12-1.96 (1H, m); δ$_C$ (101 MHz, CD$_3$OD) 160.40 (1C, d, J$_{C-F}$ 250.0), 160.06, 159.57, 159.46, 142.39 (1C, d, J$_{C-F}$ 5.5), 133.67, 131.23, 127.71, 125.00 (1C, d, J$_{C-F}$ 3.8), 124.05 (1C, d, J$_{C-F}$ 17.8), 117.86, 116.61 (1C, d, J$_{C-F}$ 22.4), 69.44, 67.02, 46.95, 28.59; HRMS (ESI): m/z 410.0947 (M+H)$^+$; calc. for C$_{18}$H$_{19}$Cl$_2$FN$_5$O: 410.0951

1-(3-(4-Chlorophenoxy)propyl)-6-(3-chlorophenyl)-1,6-dihydro-1,3,5-triazine-2,4-diamine hydrochloride. δ$_H$ (400 MHz, CD$_3$OD) 7.52 (2H, ddd, J 0.9, 1.9, 4.2), 7.47 (1H, d, J 1.1), 7.43-7.37 (1H, m), 7.35-7.29 (2H, m), 7.00-6.94 (2H, m), 5.85 (1H, d, J 2.3), 4.22-4.03 (2H, m), 3.90-3.78 (1H, m), 3.49-3.35 (1H, m), 2.30-2.16 (1H, m), 2.16-2.02 (1H, m); δ$_C$ (101 MHz, CD$_3$OD) 160.09, 159.58, 159.50, 143.43, 137.12, 133.02, 131.85, 131.29, 128.30, 127.76, 126.52, 117.80, 70.02, 66.88, 46.69, 28.52; HRMS (ESI): m/z 392.1041 (M+H)$^+$; calc. for C$_{18}$H$_{20}$Cl$_2$N$_5$O: 392.1045

1-(3-(4-Chlorophenoxy)propyl)-6-(4-fluorophenyl)-1,6-dihydro-1,3,5-triazine-2,4-diamine hydrochloride. δ$_H$ (400 MHz, CD$_3$OD) 7.53-7.45 (2H, m), 7.36-7.29 (2H, m), 7.29-7.21 (2H, m), 6.99-6.93 (2H, m), 5.82 (1H, s), 4.13-4.04 (2H, m), 3.82-3.71 (1H, m), 3.45-3.40 (1H, m), 2.26-2.12 (1H, m), 2.12-1.99 (1H, m); δ$_C$ (101 MHz, CD$_3$OD) 165.71 (1C, d, J$_{C-F}$ 247.9), 160.03, 159.55, 159.49, 137.33 (1C, d, J$_{C-F}$ 3.2), 131.28, 130.52 (2C, d, J$_{C-F}$ 8.7), 127.74, 118.13 (2C, d, J$_{C-F}$ 22.2), 117.80, 70.15, 66.86, 46.40, 28.44; HRMS (ESI): m/z 376.1334 (M+H)$^+$; calc. for C$_{18}$H$_{20}$ClFN$_5$O: 376.1340

1-(3-(4-Chlorophenoxy)propyl)-6-(2-fluorophenyl)-1,6-dihydro-1,3,5-triazine-2,4-diamine hydrochloride. δ$_H$ (400 MHz, CD$_3$OD) 7.51 (1H, dddd, J 1.8, 5.4, 7.3, 8.2), 7.38 (1H, td, J 1.7, 7.6), 7.33-7.20 (4H, m), 6.99-6.86 (2H, m), 6.11 (1H, s), 4.11-4.04 (2H, m), 3.78 (1H, ddd, J 5.8, 7.5, 15.3), 3.42-3.35 (1H, m), 2.26-1.98 (2H, m); δ$_C$ (101 MHz, CD$_3$OD) 162.58 (1C, d, J$_{C-F}$ 247.6), 160.07, 159.62, 159.47, 133.93 (1C, d, J$_{C-F}$ 8.6), 131.25, 129.61 (1C, d, J$_{C-F}$ 3.1), 127.78 (1C, d, J$_{C-F}$ 12.7), 127.76, 127.11 (1C, d, J$_{C-F}$ 3.6), 118.29 (1C, d, J$_{C-F}$ 21.4), 117.87, 66.91, 66.00 (1C, d, J$_{C-F}$ 3.9), 46.49, 28.45; HRMS (ESI): m/z 376.1341 (M+H)$^+$; calc. for C$_{18}$H$_{20}$ClFN$_5$O: 376.1340

1-(3-(4-Chlorophenoxy)propyl)-6-(2-(trifluoromethyl)phenyl)-1,6-dihydro-1,3,5-triazine-2,4-diamine hydrochloride. δ$_H$ (400 MHz, CD$_3$OD) 7.83 (2H, dd, J 7.6, 15.7), 7.68 (2H, t, J 7.4), 7.28 (2H, d, J 8.7), 6.90 (2H, d, J 8.8), 6.16 (1H, s), 4.12-3.97 (2H, m), 3.70 (1H, ddd, J 5.5, 7.7, 15.5), 3.27-3.16 (1H, m), 2.18 (1H, dqd, J 4.3, 7.2, 14.4), 2.08-1.94 (1H, m); δ$_C$ (101 MHz, CD$_3$OD) 160.28, 159.38, 159.07, 140.18, 136.02, 132.45, 131.23, 129.61, 129.40 (1C, q, J$_{C-F}$ 30.7), 128.40 (1C, q, J$_{C-F}$ 5.7), 127.74, 126.33 (1C, q, J$_{C-F}$ 273.6), 117.7066.97 (1C, q, J$_{C-F}$ 2.3), 66.79, 46.67, 28.10; HRMS (ESI): m/z 426.1239 (M+H)$^+$; calc. for C$_{19}$H$_{20}$ClF$_3$N$_5$O: 426.1308

1-(3-(3,4-Dichlorophenoxy)propyl)-6-(4-(trifluoromethyl)phenyl)-1,6-dihydro-1,3,5-triazine-2,4-diamine hydrochloride. δ$_H$ (400 MHz, CD$_3$OD) 7.82-7.76 (2H, m), 7.63 (2H, d, J 8.2), 7.42 (1H, dd, J 0.5, 8.9), 7.13 (1H, d, J 2.9), 6.93-6.89 (1H, m), 5.94 (1H, s), 4.16-4.04 (2H, m), 3.85 (1H, ddd, J 6.1, 7.5, 15.3), 3.46-3.35 (1H, m), 2.27-2.01 (2H, m); δ$_C$ (101 MHz, CD$_3$OD) 160.13, 160.10, 159.63, 145.39, 134.66, 133.60 (1C, q, J$_{C-F}$ 32.4), 132.88, 128.94, 128.26 (2C, q, J$_{C-F}$ 3.8), 126.14 (1C, q, J$_{C-F}$ 271.4), 125.89, 118.35, 116.71, 69.92, 67.37, 46.86, 28.43; HRMS (ESI): m/z 460.0908 (M+H)$^+$; calc. for C$_{19}$H$_{19}$Cl$_2$F$_3$N$_5$O: 460.0919

1-(3-(3,4-Dichlorophenoxy)propyl)-6-(2-(trifluoromethyl)phenyl)-1,6-dihydro-1,3,5-triazine-2,4-diamine hydrochloride. δ$_H$ (400 MHz, CD$_3$OD) 7.89-7.76 (2H, m), 7.69 (2H, d, J 7.9), 7.42 (1H, dd, J 2.0, 8.9), 7.08 (1H, d, J 2.1), 6.90-6.79 (1H, m), 6.16 (1H, s), 4.14-3.98 (2H, m), 3.76-3.61 (1H, m), 3.21 (1H, td, J 7.9, 15.3), 2.25-2.09 (1H, m), 2.09-1.92 (1H, m); δ$_C$ (101 MHz, CD$_3$OD) 160.24, 159.88, 159.04, 140.13, 136.03, 134.61, 132.86, 132.48, 129.62, 129.55 (1C, q, J$_{C-F}$ 5.2), 128.38 (1C, q, J$_{C-F}$ 5.8), 126.32 (1C, q, J$_{C-F}$ 273.6), 125.88, 118.22, 116.62, 67.17, 66.96, 46.56, 27.91; HRMS (ESI): m/z 460.0883 (M+H)$^+$; calc. for C$_{19}$H$_{19}$Cl$_2$F$_3$N$_5$O: 460.0919

1-(3-(3,4-Dichlorophenoxy)propyl)-6-(2-fluorophenyl)-1,6-dihydro-1,3,5-triazine-2,4-diamine hydrochloride. δ$_H$ (400 MHz, CD$_3$OD) 7.51 (1H, tdd, J 1.7, 5.4, 7.3), 7.44 (1H, d, J 8.9), 7.37 (1H, td, J 1.8, 7.5), 7.33-7.21 (2H, m), 7.14 (1H, d, J 2.9), 7.00-6.88 (1H, m), 6.10 (1H, s), 4.09 (2H, t, J 5.8), 3.77 (1H, ddd, J 5.8, 7.5, 15.3), 3.39 (1H, t, J 7.4), 2.25-2.12 (1H, m), 2.05 (1H, qd, J 5.9, 12.6); $\delta_C$ (101 MHz, CD$_3$OD) 162.59 (1C, d, J$_{C-F}$ 247.4), 160.09, 160.05, 159.63, 134.66, 133.94 (1C, d, J$_{C-F}$ 8.5), 132.88, 129.51 (1C, d, J$_{C-F}$ 3.2), 127.82 (1C, d, J$_{C-F}$ 12.7), 127.12 (1C, d, J$_{C-F}$ 3.6), 125.91, 118.33, 118.30 (1C, d, J$_{C-F}$ 21.3), 117.80, 116.73, 67.26, 65.91 (1C, d, J$_{C-F}$ 3.9), 46.41, 28.28; HRMS (ESI): m/z 410.0926 (M+H)$^+$; calc. for C$_{18}$H$_{19}$Cl$_2$FN$_5$O: 410.0951

1-(3-(3,4-Dichlorophenoxy)propyl)-6-(4-fluorophenyl)-1,6-dihydro-1,3,5-triazine-2,4-diamine hydrochloride. $\delta_H$ (400 MHz, CD$_3$OD) 7.49-7.40 (3H, m), 7.25-7.17 (2H, m), 7.12 (1H, d, J 2.9), 6.90 (1H, dd, J 2.8, 8.8), 5.80 (1H, s), 4.15-3.98 (2H, m), 3.73 (1H, ddd, J 4.8, 8.6, 11.2), 3.40-3.35 (1H, m), 2.25-1.93 (2H, m); $\delta_C$ (101 MHz, CD$_3$OD) 165.71 (1C, d, J$_{C-F}$ 248.0), 160.05 (2C), 159.54, 137.31 (1C, d, J$_{C-F}$ 3.6), 134.66, 132.87, 130.52 (2C, d, J$_{C-F}$ 8.6), 125.90, 118.32, 118.13 (2C, d, J$_{C-F}$ 22.2), 116.70, 70.14, 67.33, 46.36, 28.28; HRMS (ESI): m/z 410.0897 (M+H)$^+$; calc. for C$_{18}$H$_{19}$Cl$_2$FN$_5$O: 410.0951

6-(4-Chloro-3-fluorophenyl)-1-(3-(3,4-dichlorophenoxy)propyl)-1,6-dihydro-1,3,5-triazine-2,4-diamine hydrochloride. $\delta_H$ (400 MHz, CD$_3$OD) 7.60 (1H, t, J 7.9), 7.43 (1H, d, J 8.9), 7.35-7.28 (1H, m), 7.28-7.22 (1H, m), 7.13 (1H, d, J 2.9), 6.91 (1H, dd, J 2.9, 8.9), 5.85 (1H, s), 4.17-3.99 (2H, m), 3.88-3.75 (1H, m), 3.47-3.35 (1H, m), 2.27-1.98 (4H, m); HRMS (ESI): m/z 444.0529 (M+H)$^+$; calc. for C$_{18}$H$_{18}$Cl$_3$FN$_5$O: 444.0561

6-(2-Chlorophenyl)-1-(3-(3,4-dichlorophenoxy)propyl)-1,6-dihydro-1,3,5-triazine-2,4-diamine hydrochloride. $\delta_H$ (400 MHz, CD$_3$OD) 7.65-7.35 (4H, m), 7.33-7.21 (1H, m), 7.11 (1H, d, J 2.9), 7.00-6.86 (1H, m), 6.20 (1H, s), 4.20-4.00 (2H, m), 3.85-3.71 (1H, m), 3.32-3.24 (1H, m), 2.32-2.12 (1H, m), 2.11-1.94 (1H, m); $\delta_C$ (101 MHz, CD$_3$OD) 160.25, 159.97, 159.46, 137.57, 134.65, 134.63, 133.35, 132.86, 132.63, 130.10, 129.68, 125.92, 118.43, 116.74, 68.29, 67.27, 46.47, 28.23; HRMS (ESI): m/z 426.0598 (M+H)$^+$; calc. for C$_{18}$H$_{19}$Cl$_3$FN$_5$O: 426.0655

1-(3-(4-Chlorophenoxy)propyl)-6-(4-chlorophenyl)-1,6-dihydro-1,3,5-triazine-2,4-diamine hydrochloride. $\delta_H$ (400 MHz, CD$_3$OD) 7.49 (2H, d, J 8.5), 7.41 (2H, d, J 8.6), 7.29 (2H, d, J 8.9), 6.93 (2H, d, J 9.0), 5.80 (1H, s), 4.11-4.00 (2H, m), 3.76 (1H, ddd, J 5.9, 7.6, 15.3), 3.39 (1H, dt, J 4.2, 7.5), 2.25-2.09 (1H, m), 2.09-1.95 (1H, m); $\delta_C$ (101 MHz, CD$_3$OD) 160.05, 159.57, 159.48, 139.92, 137.64, 131.43, 131.28, 129.93, 127.74, 117.81, 70.11, 66.86, 46.57, 28.48; HRMS (ESI): m/z 392.1017 (M+H)$^+$; calc. for C$_{18}$H$_{20}$Cl$_2$N$_5$O: 392.1045

6-(3-Chloro-2-fluorophenyl)-1-(3-(4-chlorophenoxy)propyl)-1,6-dihydro-1,3,5-triazine-2,4-diamine hydrochloride. $\delta_H$ (400 MHz, CD$_3$OD) 7.64-7.54 (1H, m), 7.36-7.20 (4H, m), 6.94 (2H, d, J 9.0), 6.14 (1H, s), 4.12-4.05 (2H, m), 3.81 (1H, ddd, J 5.9, 7.5, 15.4), 3.39 (1H, dd, J 7.5, 15.2), 2.26-2.14 (1H, m), 2.12-2.00 (1H, m); $\delta_C$ (101 MHz, CD$_3$OD) 160.07, 159.54, 159.43, 157.92 (1C, d, J$_{C-F}$ 250.2), 134.18, 131.26, 129.69 (1C, d, J$_{C-F}$ 12.8), 128.09 (1C, d, J$_{C-F}$ 2.8), 127.77, 127.75 (1C, d, J$_{C-F}$ 4.9), 123.88 (1C, d, J$_{C-F}$ 17.5), 117.83, 66.87, 66.02 (1C, d, J$_{C-F}$ 3.7), 46.67, 28.44; HRMS (ESI): m/z 410.0937 (M+H)$^+$; calc. for C$_{18}$H$_{19}$Cl$_2$FN$_5$O: 410.0951

6-(4-Chlorophenyl)-1-(3-(3,4-dichlorophenoxy)propyl)-1,6-dihydro-1,3,5-triazine-2,4-diamine hydrochloride. $\delta_H$ (400 MHz, CD$_3$OD) 7.48 (2H, d, J 8.5), 7.45-7.38 (3H, m), 7.12 (1H, d, J 2.8), 7.00-6.83 (1H, m), 5.82 (1H, s), 4.15-3.99 (2H, m), 3.77 (1H, dt, J 14.0), 3.43-3.29 (1H, m), 2.25-2.10 (1H, m), 2.10-1.95 (1H, m); $\delta_C$ (101 MHz, CD$_3$OD) 160.10, 160.06, 159.60, 139.81, 137.65, 134.65, 132.85, 131.39, 129.96, 125.91, 118.43, 116.74, 70.05, 67.44, 46.60, 28.39; HRMS (ESI): m/z 426.0611 (M+H)$^+$; calc. for C$_{18}$H$_{19}$Cl$_3$FN$_5$O: 426.0655

6-(3-Chloro-2-fluorophenyl)-1-(3-(3,4-dichlorophenoxy)propyl)-1,6-dihydro-1,3,5-triazine-2,4-diamine hydrochloride. $\delta_H$ (400 MHz, CD$_3$OD) 7.60 (1H, td, J 2.6, 7.3), 7.43 (1H, d, J 8.9), 7.35-7.26 (2H, m), 7.13 (1H, d, J 2.9), 6.92 (1H, dd, J 2.9, 8.9), 6.14 (1H, s), 4.14-4.05 (2H, m), 3.81 (1H, ddd, J 6.0, 7.6, 15.3), 3.44-3.35 (1H, m), 2.29-2.14 (1H, m), 2.14-1.98 (1H, m); $\delta_C$ (101 MHz, CD$_3$OD) 160.11, 160.04, 159.56, 157.93 (1C, d, J$_{C-F}$ 249.9), 134.67, 134.18, 132.89, 129.78 (1C, d, J$_{C-F}$ 12.7), 128.00 (1C, d, J$_{C-F}$ 2.7), 127.75 (1C, d, J$_{C-F}$ 4.7), 125.92, 123.89 (1C, d, J$_{C-F}$ 17.4), 118.32, 116.70, 67.25, 65.93 (1C, d, J$_{C-F}$ 2.5), 46.60, 28.32; HRMS (ESI): m/z 444.0539 (M+H)$^+$; calc. for C$_{18}$H$_{18}$Cl$_3$FN$_5$O: 444.0561

1-(3-(4-Chlorophenoxy)propyl)-6-(2,5-dichlorophenyl)-1,6-dihydro-1,3,5-triazine-2,4-diamine hydrochloride. $\delta_H$ (400 MHz, CD$_3$OD) 7.63-7.38 (2H, m), 7.44-7.15 (3H, m), 6.94 (2H, dd, J 3.2, 9.0), 6.17 (1H, d, J 3.3), 4.23-3.98 (2H, m), 3.85-3.71 (1H, m), 3.41-3.22 (1H, m), 2.33-1.93 (2H, m); $\delta_C$ (101 MHz, CD$_3$OD) 160.27, 159.47, 159.42, 139.49, 135.88, 134.27, 133.34, 133.17, 131.29, 129.56, 127.86, 117.85, 68.16, 66.79, 46.63, 28.39; HRMS (ESI): m/z 426.0631 (M+H)$^+$; calc. for C$_{18}$H$_{19}$Cl$_3$FN$_5$O: 426.0655

1-(3-(4-Chlorophenoxy)propyl)-6-(2-fluoro-3-methoxyphenyl)-1,6-dihydro-1,3,5-triazine-2,4-diamine hydrochloride. $\delta_H$ (400 MHz, CD$_3$OD) 7.28 (2H, d, J 8.1), 7.21 (2H, d, J 6.2), 7.10-6.74 (3H, m), 6.10 (1H, s), 4.06 (2H, t, J 5.4), 3.92 (3H, s), 3.82-3.70 (1H, m), 3.47-3.34 (1H, m), 2.30-1.95 (2H, m); $\delta_C$ (101 MHz, CD$_3$OD) 160.09, 159.65, 159.48, 152.20 (1C, d, J$_{C-F}$ 248.4), 150.60 (1C, d, J$_{C-F}$ 10.1), 131.25, 128.69 (1C, d, J$_{C-F}$ 8.7), 127.76, 127.07 (1C, d, J$_{C-F}$ 4.9), 119.94, 117.86, 116.99, 66.86, 65.79 (1C, d, J$_{C-F}$ 5.1), 57.80, 46.45, 28.44; HRMS (ESI): m/z 406.1435 (M+H)$^+$; calc. for C$_{19}$H$_{22}$ClFN$_5$O$_2$: 406.1446

1-(3-(4-Chlorophenoxy)propyl)-6-(2,4-difluorophenyl)-1,6-dihydro-1,3,5-triazine-2,4-diamine hydrochloride. $\delta_H$ (400 MHz, CD$_3$OD) 7.41 (1H, td, J 6.1, 8.6), 7.29 (2H, d, J 9.1), 7.15 (1H, ddd, J 2.6, 7.0, 11.6), 7.10 (1H, tdd, J 1.1, 2.5, 8.6), 6.94 (2H, d, J 9.1), 6.07 (1H, s), 4.08 (2H, t, J 5.7), 3.76 (1H, ddd, J 5.7, 7.6, 15.4), 3.39 (1H, t, J 7.5), 2.26-2.11 (1H, m), 2.11-1.97 (1H, m). $\delta_C$ (101 MHz, CD$_3$OD) 166.06 (1C, dd, J 12.3, 250.8), 162.96 (1C, dd, J 12.4, 250.5), 160.02, 159.55, 159.45, 131.28, 131.11 (1C, dd, J 4.9, 10.2), 127.76, 124.35 (1C, dd, J 3.9, 13.1), 117.79, 114.18 (1C, dd, J 3.6, 21.9), 106.74 (1C, dd, J 25.9, 25.9), 66.77, 65.70, 46.42, 28.40. HRMS (ESI): m/z 394.1209 (M+H)$^+$; calc. For C$_{18}$H$_{19}$ClF$_2$N$_5$O: 394.1246

1-(3-(4-Chlorophenoxy)propyl)-6-(2,4-dichlorophenyl)-1,6-dihydro-1,3,5-triazine-2,4-diamine hydrochloride. $\delta_H$ (400 MHz, CD$_3$OD) 7.70-7.55 (1H, m), 7.53-7.43 (1H, m), 7.37C (1H, dd, J 4.9, 8.4), 7.32-7.23 (2H, m), 6.93 (2H, dd, J 4.9, 8.8), 6.18 (1H, d, J 4.7), 4.22-3.97 (2H, m), 3.84-3.71 (1H, m), 3.33-3.25 (1H, m), 2.30-1.91 (2H, m); $\delta_C$ (101 MHz, CD$_3$OD) 160.21, 159.44, 159.37, 138.41, 136.55, 135.58, 132.32, 131.27, 130.96, 130.37, 127.80, 117.85, 67.99, 66.80, 46.60, 28.37; HRMS (ESI): m/z 426.0643 (M+H)$^+$; calc. for C$_{18}$H$_{19}$Cl$_3$FN$_5$O: 426.0655

1-(3-(4-Chlorophenoxy)propyl)-6-(3-(trifluoromethoxy)phenyl)-1,6-dihydro-1,3,5-triazine-2,4-diamine hydrochloride. $\delta_H$ (400 MHz, CD$_3$OD) 7.61 (1H, t, J 8.0), 7.42 (2H, dd, J 8.0, 17.5), 7.33 (1H, s), 7.31-7.23 (2H, m), 7.01-6.88 (2H, m), 5.89 (1H, s), 4.21-3.99 (2H, m), 3.91-3.73 (1H, m), 3.46-3.32 (1H, m), 2.33-1.95 (2H, m); $\delta_C$ (101 MHz, CD$_3$OD) 160.09, 159.58, 159.50, 151.82, 143.84, 133.30, 131.24, 127.67, 126.91, 124.10, 122.68 (1C, q, J$_{C-F}$ 256.3), 120.84, 117.79, 69.76, 66.91, 46.85, 28.58; HRMS (ESI): m/z 442.1222 (M+H)+; calc. for $C_{19}H_{20}ClF_3N_5O_2$: 442.1258

1-(3-(4-Chlorophenoxy)propyl)-6-m-tolyl-1,6-dihydro-1,3,5-triazine-2,4-diamine hydrochloride. $\delta_H$ (400 MHz, CD$_3$OD) 6.99 (1H, t, J 7.5), 6.92 (3H, d, J 8.7), 6.83 (2H, d, J 12.0), 6.55 (2H, d, J 8.9), 5.34 (1H, s), 3.80-3.60 (2H, m), 3.41-3.26 (1H, m), 3.10-2.88 (1H, m), 2.02 (3H, s), 1.84-1.58 (2H, m); $\delta_C$ (101 MHz, CD$_3$OD) 160.61, 159.51 (2C), 147.82, 141.46, 141.05, 132.53, 131.28, 131.26, 128.77, 127.75, 125.31, 117.82, 70.92, 66.90, 46.33, 28.46, 22.32; HRMS (ESI): m/z 372.1570 (M+H)+; calc. for $C_{19}H_{23}ClN_5O$: 372.1591

1-(3-(4-Chlorophenoxy)propyl)-6-(4-(trifluoromethylthio)phenyl)-1,6-dihydro-1,3,5-triazine-2,4-diamine hydrochloride. $\delta_H$ (400 MHz, CD$_3$OD) 7.81 (2H, d, J 8.2), 7.55 (2H, d, J 8.2), 7.29 (2H, d, J 7.3), 6.94 (2H, d, J 6.9), 5.89 (1H, s), 4.21-3.97 (2H, m), 3.92-3.76 (1H, m), 3.46-3.31 (1H, m), 2.27-2.13 (1H, m), 2.13-1.98 (1H, m); $\delta_C$ (101 MHz, CD$_3$OD) 160.08, 159.58, 159.49, 144.39, 139.15, 131.27, 129.49, 129.08 (1C, q, $J_{C-F}$ 257.6), 127.70, 117.81, 69.92, 66.87, 46.88, 28.54; HRMS (ESI): m/z 458.1006 (M+H)+; calc. for $C_{19}H_{20}ClF_3N_5OS$: 458.1029

1-(3-(2-Methoxy-4-methylphenoxy)propyl)-6-phenyl-1,6-dihydro-1,3,5-triazine-2,4-diamine hydrochloride. $\delta_H$ (400 MHz, CD$_3$OD) 7.57-7.46 (3H, m), 7.46-7.37 (2H, m), 6.86 (2H, d, J 8.2), 6.75-6.68 (1H, m), 5.83 (1H, s), 4.09-3.96 (2H, m), 3.85 (3H, s), 3.72-3.59 (1H, m), 3.56-3.37 (1H, m), 2.31 (3H, s), 2.13-1.89 (2H, m); $\delta_C$ (101 MHz, CD$_3$OD) 160.02, 159.61, 151.33, 147.53, 141.43, 133.56, 131.83, 131.32, 128.29, 123.02, 115.59, 114.77, 71.03, 67.35, 57.10, 46.27, 28.81, 21.94; HRMS (ESI): m/z 368.2051 (M+H)+; calc. for $C_{20}H_{26}N_5O_2$: 368.2087

1-(3-(4-Bromophenoxy)propyl)-6-phenyl-1,6-dihydro-1,3,5-triazine-2,4-diamine hydrochloride. $\delta_H$ (400 MHz, CD$_3$OD) 7.57-7.33 (7H, m), 6.97-6.79 (2H, m), 5.76 (1H, s), 4.16-3.95 (2H, m), 3.73 (1H, ddd, J 5.9, 7.6, 15.3), 3.51-3.19 (1H, m), 2.23-1.93 (2H, m); $\delta_C$ (101 MHz, CD$_3$OD) 160.07, 159.99, 159.62, 141.16, 134.27, 131.77, 131.30, 128.22, 118.34, 114.86, 70.74, 66.82, 46.42, 28.47; HRMS (ESI): m/z 402.0891 (M+H)+; calc. for $C_{18}H_{21}BrN_5O$: 402.0929

1-(3-(4-Chloro-3-fluorophenoxy)propyl)-6-phenyl-1,6-dihydro-1,3,5-triazine-2,4-diamine hydrochloride. $\delta_H$ (400 MHz, CD$_3$OD) 7.52-7.45 (3H, m), 7.43 (2H, dt, J 3.6, 5.0), 7.37 (1H, t, J 8.8), 6.87 (1H, dd, J 2.8, 11.1), 6.78 (1H, ddd, J 1.2, 2.8, 8.9), 5.79 (1H, s), 4.12-4.01 (2H, m), 3.80-3.70 (1H, m), 3.41-3.30 (1H, m), 2.22-2.10 (1H, m), 2.10-1.97 (1H, m); $\delta_C$ (101 MHz, CD$_3$OD) 160.84 (1C, d, $J_{C-F}$ 9.9), 160.57 (1C, d, $J_{C-F}$ 246.6), 160.09, 159.61, 141.08, 132.72 (1C, d, $J_{C-F}$ 1.0), 131.84, 131.31, 128.24, 114.06 (1C, d, $J_{C-F}$ 17.9), 113.48 (1C, d, $J_{C-F}$ 3.3), 105.30 (1C, d, $J_{C-F}$ 24.6), 70.77, 67.43, 46.41, 28.31; HRMS (ESI): m/z 376.1312 (M+H)+; calc. for $C_{18}H_{20}ClFN_5O$: 376.1340

1-(3-(3,4-Difluorophenoxy)propyl)-6-phenyl-1,6-dihydro-1,3,5-triazine-2,4-diamine hydrochloride. $\delta_H$ (400 MHz, CD$_3$OD) 7.59-7.35 (5H, m), 7.27-7.12 (1H, m), 6.98-6.82 (1H, m), 6.74 (1H, ddd, J 1.7, 3.0, 5.7), 5.79 (1H, s), 4.10-3.97 (2H, m), 3.82-3.70 (1H, m), 3.42-3.30 (1H, m), 2.22-2.09 (1H, m), 2.02 (1H, qd, J 5.7, 12.5); $\delta_C$ (101 MHz, CD$_3$OD) 160.09, 159.61, 157.33 (1C, dd, $J_{C-F}$ 2.2, 8.8), 152.55 (1C, dd, $J_{C-F}$ 13.9, 245.8), 147.15 (1C, dd, $J_{C-F}$ 12.9, 238.7), 141.08, 131.82, 131.31, 128.24, 119.25 (1C, dd, $J_{C-F}$ 1.4, 18.7), 112.08 (1C, dd, $J_{C-F}$ 1.8, 3.6), 105.91 (1C, d, $J_{C-F}$ 20.5), 70.75, 67.52, 46.44, 28.41; HRMS (ESI): m/z 360.1607 (M+H)+; calc. for $C_{18}H_{20}F_2N_5O$: 360.1636

1-(5-(4-Chlorophenoxy)pentyl)-6-(4-(trifluoromethyl)phenyl)-1,6-dihydro-1,3,5-triazine-2,4-diamine hydrochloride. $\delta_H$ (400 MHz, CD$_3$OD) 7.80 (2H, d, J 8.4), 7.61 (2H, d, J 8.2), 7.26 (2H, d, J 8.6), 6.89 (2H, d, J 8.7), 5.92 (1H, s), 3.97 (2H, t, J 6.1), 3.64 (1H, ddd, J 5.4, 9.1, 14.9), 3.19 (1H, ddd, J 6.1, 9.0, 15.1), 1.92-1.48 (6H, m). $\delta_C$ (101 MHz, CD$_3$OD) 159.93, 159.89, 159.56, 145.38, 133.32 (1C, q, $J_{C-F}$ 32.3), 131.08 (2C), 128.85 (2C), 128.07 (2C, q, $J_{C-F}$ 3.7), 127.08, 126.07 (1C, q, $J_{C-F}$ 271.5), 117.74, 69.71, 69.52, 41.51, 30.67, 28.77, 24.82. HRMS (ESI): m/z 454.1630 (M+H)+; calc. for $C_{21}H_{24}ClF_3N_5O$: 454.1621

EXAMPLE 2

Bioavailability and Efficacy In Vivo

The bioavailability properties were evaluated in a mouse model. The animals utilized were male C57 BL6 mice, weighing approximately 20-25 g. The compound was administered orally (N=10) to mice at 50 mg/kg in a mixture of water and DMSO (90:10). The total volume per administration was 200 μl. Blood samples (30 μl) were collected before and at 0.25, 1, 2, 3 and 4 hours after administration of the test medication by tail tip bleeding into the extraction buffer and were stored at −20° C. The compound was also administered intravenously (N=10) at 5 mg/kg in the same solvent as described above. The compound (200 μl) was injected into the dorsal penis vein. The animals were anaesthetized (Ketamine, 120 mg/kg and Xylazine, 16 mg/kg) for the intravenous injection procedure. Blood samples (30 μl) were collected at 0, 5 min, 1, 2, 3, 5 and 7 hours after administration of the test medication by tail tip bleeding into the extraction buffer and were stored at −20° C. The study samples were analysed using an LC/MS/MS assay, and revealed levels of 5.3±1.2 ng/ml to 6.3±2.2 ng/ml in the blood after oral administration at 50 mg/kg or 5 mg/kg.

The same compound was evaluated in a mouse model of malaria for in vivo efficacy following preliminary in vitro and pharmacokinetic testing. The compound was administered at two different doses using the 4-day suppressive test model. The compound was administered orally at 50 mg/kg and 5 mg/kg. Each dose was made up in a combination of water and DMSO immediately prior to treatment. The two groups of control animals for the experiment were treated orally with water/DMSO alone and chloroquine administered orally at a suppressive, but not lethal, dose of 5 mg/kg. Samples were taken at pre-determined time points in order to evaluate parasitaemia.

The animals utilised were male C57 BL6 mice, weighing approximately 20-30 g at the start of the procedure. Animals were infected with 1×10$^7$ parasitised erythrocytes and treated at predetermined time points over 4 days. Physical examinations were conducted daily; animal weight was determined daily until Day 7 and intermittently after that until only the positive controls remained and the experiment was ended. Parasite level was monitored at Day 1, 4, 7, 10 and 15. The parasite used was the chloroquine (CQ)-sensitive isolate *Plasmodium berghei*, a highly virulent and lethal strain of malaria and a suitable model system for the tests described herein. Parasites were maintained in host animals until such time as the amount was sufficient to infect all the test animals on the same day.

Two host mice were infected with parasites and left untreated to allow the parasites to multiply. Parasitemia was monitored occasionally until it was sufficiently high; at that time, parasites were harvested from the host mice via cardiac puncture.

The two parasite stocks were pooled and average parasitemia of the pooled stock was determined microscopically. Additionally, the total number of erythrocytes per milliliter of the pooled stock was determined; this is necessary in order to ensure test animals obtain both uniform and correct amounts of parasite to establish the infection. Test mice were divided into four groups of five animals and weighed.

Parasitised erythrocytes (pRBC) were transferred to microfuge tubes and maintained in phosphate-buffered saline at a level of $5 \times 10^7$ pRBC/ml as a secondary stock. 200 µl of the secondary stock was injected into the peritoneum of each test animal in order to introduce $1 \times 10^7$ pRBC to each mouse. Immediately thereafter, the mice in each group were treated with the predetermined regimen for that group (table 1). Treatments were repeated 24, 48, and 72 hours after infection. Additionally, weights were also determined at each of these times. Fresh stocks of each drug were made immediately before treatment commenced. Injected volume was 200 µl administered orally via a gavage tube. Parasitemia was determined microscopically using Giemsa-stained blood smears made from each animal.

The results are shown in FIG. 4 below. As shown, a similar recrudescence pattern to chloroquine is observed for both the high and low doses of the compound studied. The mouse of the control group with the highest level of parasitaemia died before analysis on day 10 as shown in FIG. 5, thus artificially reducing the level of parasitaemia of the control group after this point.

REFERENCES

1. I M Kompis, K Islam and R L Then, *Chem. Rev.*, 2005, 105, 593-620.
2. G Rastelli, W Sirawaraporn, P Sompornpisut, T Vilaivan, S Kamchonwongpaisan, R Quarrell, G Lowe, Y Thebtaranonth and Y Yuthavong, *Bioorg. Med. Chem.*, 2000, 8, 1117-1128.
3. Y Yuthavong, *Microbes and Infection*, 2002, 4, 175-182.
4. D C Warhurst, *Drug Discovery Today*, 1998, 3, 538-546.
5. A Mital, *Curr. Med. Chem.*, 2007, 14, 759-773.
6. S Y Hunt, C Detering, G Varani, D P Jacobus, G A Schiehser, H-M Shieh, I Nevchas, J Terpinski and C H Sibley, *Mol. Biochem. Parasitol.*, 2005, 144, 198-205.
7. N P Jensen, A L Ager, R A Bliss, C J Canfield, B M Kotecka, K H Rieckmann, J Terpinski and D P Jacobus, *J. Med. Chem.*, 2001, 44, 3925-3931.
8. H Newman, E L Moon and J P English, U.S. Pat. No. 3,287,365, 1966.
9. L Doub, U.S. Pat. No. 3,170,925, 1965.
10. a) B R Baker and B-T Ho, *J. Heterocyclic Chem.*, 1965, 2, 72-79, b) BR Baker, *J. Med. Chem.*, 1967, 10, 912-917.
11. C J Peake and S Y Lin, U.S. Pat. No. 5,565,451, 1996.
12. a) S L Shapiro, V A Parrino and L Freedman, *J. Am. Chem. Soc.*, 1959, 81, 3728-3736; b) S L Shapiro and L Freedman, 2,961,377, 1960.

The invention claimed is:

1. A method of treating malaria in a subject comprising administering to said subject a compound of formula I,

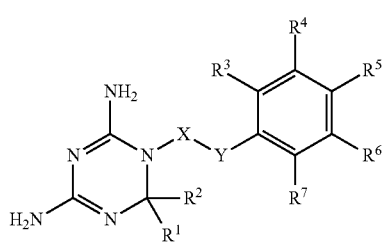

in which $R^1$ and $R^2$ are independently selected from the group consisting of H, alkyl, aryl and heteroaryl, or $R^1$ and $R^2$ together form a $C_5$-$C_7$ ring, $R^3$-$R^7$ are independently selected from the group consisting of H, halogen, alkyl and alkoxy, X is $(CH_2)_n$ in which n is 0-5, Y is selected from the group consisting of $CH_2$, $NR^8$, O or S in which $R^8$ is H or alkyl, a salt thereof and a stereoisomer thereof, in which "alkyl" means a group selected from the group consisting of:
  $C_1$-$C_7$ straight chain alkyl groups, optionally substituted with one or more F, Cl, Br, O, S or N, and
  $C_1$-$C_7$ branched alkyl groups optionally substituted with one or more F, Cl, Br, O, S or N, "aryl" means a group selected from the group consisting of:
  phenyl, and
  phenyl substituted with one or more F, Cl, Br, S, N, $C_1$-$C_7$ alkoxy, nitrile, trifluoromethyl, $C_1$-$C_7$ straight chain alkyl groups and $C_1$-$C_7$ branched alkyl groups, the alkyl groups being optionally substituted with one or more F, Cl, Br, O, S or N, "heteroaryl" means a group selected from the group consisting of thiophenyl, furyl, pyridinyl, isoxazolinyl, pyrrolinyl, oxazolinyl, thiazolinyl, imidazolyl which is optionally substituted with one or more F, Cl, Br, S, N, $C_1$-$C_7$ alkoxy, nitrile, trifluoromethyl, $C_1$-$C_7$ straight chain alkyl groups and $C_1$-$C_7$ branched alkyl groups, the alkyl groups being optionally substituted with one or more F, Cl, Br, O, S or N, "halogen" means F, Cl or Br, and "alkoxy" means a $C_1$-$C_7$ alkoxy group provided that:

(1) when $R^1$ and $R^2$ are both methyl, X is $(CH_2)_n$, n is 2-5 and Y is O, then $R^3$-$R^7$ are not all H, (2) when $R^1$ and $R^2$ are independently selected from the group consisting of H, methyl, isopropyl, propyl, cyclohexyl, phenyl, 4-fluorophenyl, 4-chlorophenyl, 3,4-methylenedioxyphenyl, 4-acetamidophenyl, 4-methylthiophenyl or $R^1$ and $R^2$ together form —(CH2)2CH(CH3)-(CH2)2—, X is $(CH2)_n$, n is 0-3 and Y is CH2, then R3-R7 are not all H;

(3) when $R^1$ and $R^2$ are both methyl, X is $CH_2$, $NR^8$ is NH, and $R^3$, $R^4$, $R^6$ and $R^7$ are H, then $R^5$ may not be Cl, F or H;

(4) when $R^1$ and $R^2$ are both methyl, X is $CH_2$, $NR^8$ is NH and $R^3$, $R^6$ and $R^7$ are H, then $R^4$ and $R^5$ may not both be Cl; and (5) when $R^1$ and $R^2$ are both methyl, X is $CH_2$ and $NR^8$ is NMe, not all of $R^3$, $R^4$, $R^5$, $R^6$, $R^7$ may be H.

2. The method as claimed in claim 1, wherein the malaria is resistant to antifolate compounds.

3. The method as claimed in claim 2, wherein the antifolate compounds are selected from the group consisting of cycloguanil and pyrimethamine.

4. A compound of formula I,

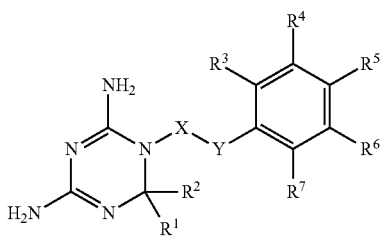

in which
R$^1$ and R$^2$ are independently selected from the group consisting of H, alkyl, aryl and heteroaryl, or R$^1$ and R$^2$ together form a C$_5$-C$_7$ ring,
R$^3$-R$^7$ are independently selected from the group consisting of H, halogen, alkyl and alkoxy,
X is (CH$_2$)$_n$ in which n is 0-5,
Y is selected from the group consisting of CH$_2$, NR$^8$, O or S in which R$^8$ is H or alkyl,
a salt thereof and a stereoisomer thereof,
in which
"alkyl" means a group selected from the group consisting of:
  C$_1$-C$_7$ straight chain alkyl groups, optionally substituted with one or more F, Cl, Br, O, S or N, and
  C$_1$-C$_7$ branched alkyl groups optionally substituted with one or more F, Cl, Br, O, S or N,
"aryl" means a group selected from the group consisting of:
  phenyl, and
  phenyl substituted with one or more F, Cl, Br, S, N, C$_1$-C$_7$ alkoxy, nitrile, trifluoromethyl, C$_1$-C$_7$ straight chain alkyl groups and C$_1$-C$_7$ branched alkyl groups, the alkyl groups being optionally substituted with one or more F, Cl, Br, O, S or N,
"heteroaryl" means a group selected from the group consisting of thiophenyl, furyl, pyridinyl, isoxazolinyl, pyrrolinyl, oxazolinyl, thiazolinyl, imidazolyl which is optionally substituted with one or more F, Cl, Br, S, N, C$_1$-C$_7$ alkoxy, nitrile, trifluoromethyl, C$_1$-C$_7$ straight chain alkyl groups and C$_1$-C$_7$ branched alkyl groups, the alkyl groups being optionally substituted with one or more F, Cl, Br, O, S or N,
"halogen" means F, Cl or Br, and
"alkoxy" means a C$_1$-C$_7$ alkoxy group provided that:
(1) when R$^1$ and R$^2$ are both methyl, X is (CH$_2$)$_n$, n is 2-5 and Y is O, then R$^3$-R$^7$ are not all H,
(2) when R$^1$ and R$^2$ are independently selected from the group consisting of H, methyl, isopropyl, propyl, cyclohexyl, phenyl, 4-fluorophenyl, 4-chlorophenyl, 3,4-methylenedioxyphenyl, 4-acetamidophenyl, 4-methylthiophenyl or R$^1$ and R$^2$ together form —(CH$_2$)$_2$CH(CH$_3$)—(CH$_2$)$_2$—, X is (CH$_2$)$_1$, n is 0-3 and Y is CH$_2$, then R$^3$-R$^7$ are not all H,
(3) when R$^1$ is selected from the group consisting of H, trifluoromethyl, undecyl, tert-butyl or phenyl and R$^2$ is H or methyl, Y is CH$_2$ for X=(CH$_2$)$_n$ and n=0 and R$^5$ is H or chlorine, then R$^3$, R$^4$, R$^6$ and R$^7$ are not all H and when R$^4$ and R$^5$ are methoxy then not all of R$^3$, R$^6$ and R$^7$ are H, and
(4) when R$^1$ and R$^2$ are both methyl, X is (CH$_2$)$_n$, n is 0-3 and Y is CH$_2$, then neither R$^3$ nor R$^7$ is H;
(5) when R$^1$ and R$^2$ are both methyl, X is CH$_2$, NR$^8$ is NH, and R$^3$, R$^4$, R$^6$ and R$^7$ are H, then R$^5$ may not be Cl, F or H;
(6) when R$^1$ and R$^2$ are both methyl, X is CH$_2$, NR$^8$ is NH and R$^3$, R$^6$ and R$^7$ are H, then R$^4$ and R$^5$ may not both be Cl; and
(7) when R$^1$ and R$^2$ are both methyl, X is CH$_2$ and NR$^8$ is NMe, not all of R$^3$, R$^4$, R$^5$, R$^6$, R$^7$ may be H.

5. A compound as claimed in claim 4, in which the salt is a salt of an acid selected from the group consisting of hydrochloric acid, picric acid, nitric acid and acetic acid.

6. A compound as claimed in claim 4, wherein:
R$^1$ is hydrogen, R$^2$ is selected from the group consisting of aryl, R$^3$ to R$^7$ are selected from the group consisting of hydrogen, halogen, alkyl and alkoxy; X is (CH$_2$)$_n$ where n is 0 or 1,
Y is methylene and R$^3$-R$^7$ cannot all be H;
R$^1$ is hydrogen, R$^2$ is selected from the group consisting of aryl, R$^3$ to R$^7$ are selected from the group consisting of hydrogen, halogen, alkyl and alkoxy; at least one of R$^3$ to R$^7$ is chlorine, X is (CH$_2$)$_n$ where n is 0 or 1 and Y represents methylene;
R$^1$ is hydrogen, R$^2$ is selected from the group consisting of aryl, R$^3$ to R$^7$ are selected from the group consisting of hydrogen, halogen, alkyl and alkoxy; X is (CH$_2$)$_n$ where n is 2 to 5 and Y is oxygen;
R$^1$ is hydrogen, R$^2$ is selected from the group consisting of aryl, R$^3$ to R$^7$ are selected from the group consisting of hydrogen, halogen, alkyl and alkoxy; at least one of R$^3$ to R$^7$ is chlorine, X is (CH$_2$)$_n$ where n is 2 to 5 and Y is oxygen;
R$^1$ and R$^2$ are independently selected from the group consisting of hydrogen, aryl and heteroaryl, R$^5$ is chlorine and R$^4$ is selected from the group consisting of hydrogen atom and chlorine, X is a straight-chain alkyl group containing up to 5 carbon atoms, and Y is selected from the group consisting of methylene, nitrogen, oxygen and sulphur;
R$^1$ and R$^2$ are selected from the group consisting of hydrogen, aryl and heteroaryl, R$^3$ to R$^7$ are selected from the group consisting of hydrogen, halogen, alkyl and alkoxy; X is (CH$_2$)$_n$ where n is 0 to 5, Y is selected form CH$_2$, O, S and NR$^8$ and R$^8$ is selected from the group consisting of hydrogen and alkyl.

7. A compound as claimed in claim 4, which is selected from the group consisting of:
1-(3,4-Dichlorobenzyl)-6-phenyl-1,6-dihydro-1,3,5-triazine-2,4-diamine hydrochloride,
1-(4-Chlorophenethyl)-6-phenyl-1,6-dihydro-1,3,5-triazine-2,4-diamine hydrochloride,
1-(3,4-Dichlorophenethyl)-6-phenyl-1,6-dihydro-1,3,5-triazine-2,4-diamine hydrochloride,
1-(2-(4-Chlorophenoxy)ethyl)-6-phenyl-1,6-dihydro-1,3,5-triazine-2,4-diamine hydrochloride,
1-(2-(3,4-Dichlorophenoxy)ethyl)-6-phenyl-1,6-dihydro-1,3,5-triazine-2,4-diamine hydrochloride,
1-(3-(4-Chlorophenoxy)propyl)-6-phenyl-1,6-dihydro-1,3,5-triazine-2,4-diamine hydrochloride,
1-(3-(3,4-Dichlorophenoxy)propyl)-6-phenyl-1,6-dihydro-1,3,5-triazine-2,4-diamine hydrochloride,
1-(3-(2,4-Dichlorophenoxy)propyl)-6-phenyl-1,6-dihydro-1,3,5-triazine-2,4-diamine hydrochloride,
6-Phenyl-1-(3-(3-(trifluoromethyl)phenoxy)propyl)-1,6-dihydro-1,3,5-triazine-2,4-diamine hydrochloride,
1-(3-(4-Methoxyphenoxy)propyl)-6-phenyl-1,6-dihydro-1,3,5-triazine-2,4-diamine hydrochloride, 1-(3-(2-Fluorophenoxy)propyl)-6-phenyl-1,6-dihydro-1,3,5-triazine-2,4-diamine hydrochloride,
1-(3-(2-Chlorophenoxy)propyl)-6-phenyl-1,6-dihydro-1,3,5-triazine-2,4-diamine hydrochloride,
1-(3-(4-Fluorophenoxy)propyl)-6-phenyl-1,6-dihydro-1,3,5-triazine-2,4-diamine hydrochloride,
6-Phenyl-1-(3-(4-(trifluoromethyl)phenoxy)propyl)-1,6-dihydro-1,3,5-triazine-2,4-diamine hydrochloride,
1-(3-(4-Chlorophenoxy)propyl)-6-(2-chlorophenyl)-1,6-dihydro-1,3,5-triazine-2,4-diamine hydrochloride,
1-(3-(4-Chlorophenoxy)propyl)-6-(4-(trifluoromethyl)phenyl)-1,6-dihydro-1,3,5-triazine-2,4-diamine hydrochloride,
1-(3-(4-Chlorophenoxy)propyl)-6-(4-methoxyphenyl)-1,6-dihydro-1,3,5-triazine-2,4-diamine hydrochloride,
6-(4-Chloro-3-fluorophenyl)-1-(3-(4-chlorophenoxy)propyl)-1,6-dihydro-1,3,5-triazine-2,4-diamine hydrochloride,
1-(3-(4-Chlorophenoxy)propyl)-6-(3-chlorophenyl)-1,6-dihydro-1,3,5-triazine-2,4-diamine hydrochloride,
1-(3-(4-Chlorophenoxy)propyl)-6-(4-fluorophenyl)-1,6-dihydro-1,3,5-triazine-2,4-diamine hydrochloride,
1-(3-(4-Chlorophenoxy)propyl)-6-(2-fluorophenyl)-1,6-dihydro-1,3,5-triazine-2,4-diamine hydrochloride,
1-(3-(4-Chlorophenoxy)propyl)-6-(2-(trifluoromethyl)phenyl)-1,6-dihydro-1,3,5-triazine-2,4-diamine hydrochloride,
1-(3-(3,4-Dichlorophenoxy)propyl)-6-(4-(trifluoromethyl)phenyl)-1,6-dihydro-1,3,5-triazine-2,4-diamine hydrochloride,
1-(3-(3,4-Dichlorophenoxy)propyl)-6-(2-(trifluoromethyl)phenyl)-1,6-dihydro-1,3,5-triazine-2,4-diamine hydrochloride,
1-(3-(3,4-Dichlorophenoxy)propyl)-6-(2-fluorophenyl)-1,6-dihydro-1,3,5-triazine-2,4-diamine hydrochloride,
1-(3-(3,4-Dichlorophenoxy)propyl)-6-(4-fluorophenyl)-1,6-dihydro-1,3,5-triazine-2,4-diamine hydrochloride,
6-(4-Chloro-3-fluorophenyl)-1-(3-(3,4-dichlorophenoxy)propyl)-1,6-dihydro-1,3,5-triazine-2,4-diamine hydrochloride,
6-(2-Chlorophenyl)-1-(3-(3,4-dichlorophenoxy)propyl)-1,6-dihydro-1,3,5-triazine-2,4-diamine hydrochloride,
1-(3-(4-Chlorophenoxy)propyl)-6-(4-chlorophenyl)-1,6-dihydro-1,3,5-triazine-2,4-diamine hydrochloride,
6-(3-Chloro-2-fluorophenyl)-1-(3-(4-chlorophenoxy)propyl)-1,6-dihydro-1,3,5-triazine-2,4-diamine hydrochloride,
6-(4-Chlorophenyl)-1-(3-(3,4-dichlorophenoxy)propyl)-1,6-dihydro-1,3,5-triazine-2,4-diamine hydrochloride,
6-(3-Chloro-2-fluorophenyl)-1-(3-(3,4-dichlorophenoxy)propyl)-1,6-dihydro-1,3,5-triazine-2,4-diamine hydrochloride,
1-(3-(4-Chlorophenoxy)propyl)-6-(2,5-dichlorophenyl)-1,6-dihydro-1,3,5-triazine-2,4-diamine hydrochloride,
1-(3-(4-Chlorophenoxy)propyl)-6-(2-fluoro-3-methoxyphenyl)-1,6-dihydro-1,3,5-triazine-2,4-diamine hydrochloride,
1-(3-(4-Chlorophenoxy)propyl)-6-(2,4-difluorophenyl)-1,6-dihydro-1,3,5-triazine-2,4-diamine hydrochloride,
1-(3-(4-Chlorophenoxy)propyl)-6-(2,4-dichlorophenyl)-1,6-dihydro-1,3,5-triazine-2,4-diamine hydrochloride,
1-(3-(4-Chlorophenoxy)propyl)-6-(3-(trifluoromethoxy)phenyl)-1,6-dihydro-1,3,5-triazine-2,4-diamine hydrochloride,
1-(3-(4-Chlorophenoxy)propyl)-6-m-tolyl-1,6-dihydro-1,3,5-triazine-2,4-diamine hydrochloride,
1-(3-(4-Chlorophenoxy)propyl)-6-(4-(trifluoromethylthio)phenyl)-1,6-dihydro-1,3,5-triazine-2,4-diamine hydrochloride,
1-(3-(2-Methoxy-4-methylphenoxy)propyl)-6-phenyl-1,6-dihydro-1,3,5-triazine-2,4-diamine hydrochloride,
1-(3-(4-Bromophenoxy)propyl)-6-phenyl-1,6-dihydro-1,3,5-triazine-2,4-diamine hydrochloride,
1-(3-(4-Chloro-3-fluorophenoxy)propyl)-6-phenyl-1,6-dihydro-1,3,5-triazine-2,4-diamine hydrochloride,
1-(3-(3,4-Difluorophenoxy)propyl)-6-phenyl-1,6-dihydro-1,3,5-triazine-2,4-diamine hydrochloride,
6-(2-Chlorophenyl)-1-(4-(3,4-dichlorophenoxy)butyl)-1,6-dihydro-1,3,5-triazine-2,4-diamine, and
(5-(4-Chlorophenoxy)pentyl)-6-(4-(trifluoromethyl)phenyl)-1,6-dihydro-1,3,5-triazine-2,4-diamine hydrochloride.

8. A pharmaceutical formulation or composition which comprises a compound as claimed in claim 4 and a pharmaceutically acceptable excipient.

9. The pharmaceutical formulation or composition of claim 8, wherein the pharmaceutically acceptable excipient comprises water and dimethyl sulfoxide (DMSO).

* * * * *

UNITED STATES PATENT AND TRADEMARK OFFICE
CERTIFICATE OF CORRECTION

PATENT NO.      : 8,940,892 B2                         Page 1 of 1
APPLICATION NO. : 13/390017
DATED           : January 27, 2015
INVENTOR(S)     : Amanda Louise Rousseau et al.

It is certified that error appears in the above-identified patent and that said Letters Patent is hereby corrected as shown below:

On the title page

In column 2 (page 1, item 56) at line 13, Under Other Publications, change "l" to --1--.

In column 2 (page 1, item 56) at line 15, Under Other Publications, change "Chemisty" to --Chemistry--.

In the specification

In column 2 at line 10, Change "pyrimethyamine.$^5$" to --pyrimethamine.$^5$--.

In column 2 at line 27, Change "composition$^5$," to --composition$^8$,--.

In column 3 at line 62, Change "form" to --from--.

In column 26 at line 3, Change "acid" to --acid.--.

In column 28 at line 3, Change "pyrimethamine," to --pyrimethamine.--.

In column 36 at lines 61-67 (approx.), Delete "The two .... weighed." and insert the same on Col. 36, line 60, after "puncture.", as a continuation of the same paragraph.

In the claims

In column 38 at line 63 (approx.), In Claim 2, change "the-malaria" to --the malaria--.

In column 39 at line 58, In Claim 4, change "$(CH_2)_1$," to --$(CH_2)_n$,--.

In column 40 at line 43, In Claim 6, change "form" to --from--.

Signed and Sealed this
Twelfth Day of January, 2016

Michelle K. Lee
*Director of the United States Patent and Trademark Office*